United States Patent [19]

Dragoo et al.

[11] Patent Number: 5,858,292
[45] Date of Patent: *Jan. 12, 1999

[54] METHOD AND APPARATUS FOR MAKING STRETCHABLE ABSORBENT ARTICLES

[75] Inventors: Jerry Layne Dragoo, Fairfield; James Edward Zorb, Cincinnati; Michael Gary Nease, Fairfield, all of Ohio

[73] Assignee: The Proctor & Gamble Company, Cincinnati, Ohio

[ * ] Notice: The term of this patent shall not extend beyond the expiration date of Pat. No. 5,560,878.

[21] Appl. No.: 650,298

[22] Filed: May 20, 1996

Related U.S. Application Data

[63] Continuation of Ser. No. 346,653, Nov. 30, 1994, Pat. No. 5,560,878.

[51] Int. Cl.[6] .................................................. B29C 70/06
[52] U.S. Cl. .......................... 264/115; 264/122; 264/518; 425/82.1; 425/83.1
[58] Field of Search ................................ 264/6, 115, 518, 264/122; 156/167; 425/72.2, 82.1, 83.1

[56] References Cited

U.S. PATENT DOCUMENTS

| | | | |
|---|---|---|---|
| 4,429,001 | 1/1984 | Kolpin et al. | 428/283 |
| 4,724,114 | 2/1988 | McFarland et al. | 264/510 |
| 4,921,645 | 5/1990 | Insley | 264/6 |

*Primary Examiner*—Mary Lynn Theisen
*Attorney, Agent, or Firm*—Harness, Dickey & Pierce, P.L.C.

[57] ABSTRACT

A method and apparatus for making stretchable absorbent diaper articles. An absorbent material is provided and entangled with a stretchable material to form a stretchable network incorporating the absorbent material. In one embodiment a plurality of foam absorbent material particulates are drawn or accelerated by gravity, vacuum or forced air through a stream of a meltblown adhesive that contacts and entangles the particulates and forms a stretchable network incorporating the particulates.

20 Claims, 7 Drawing Sheets

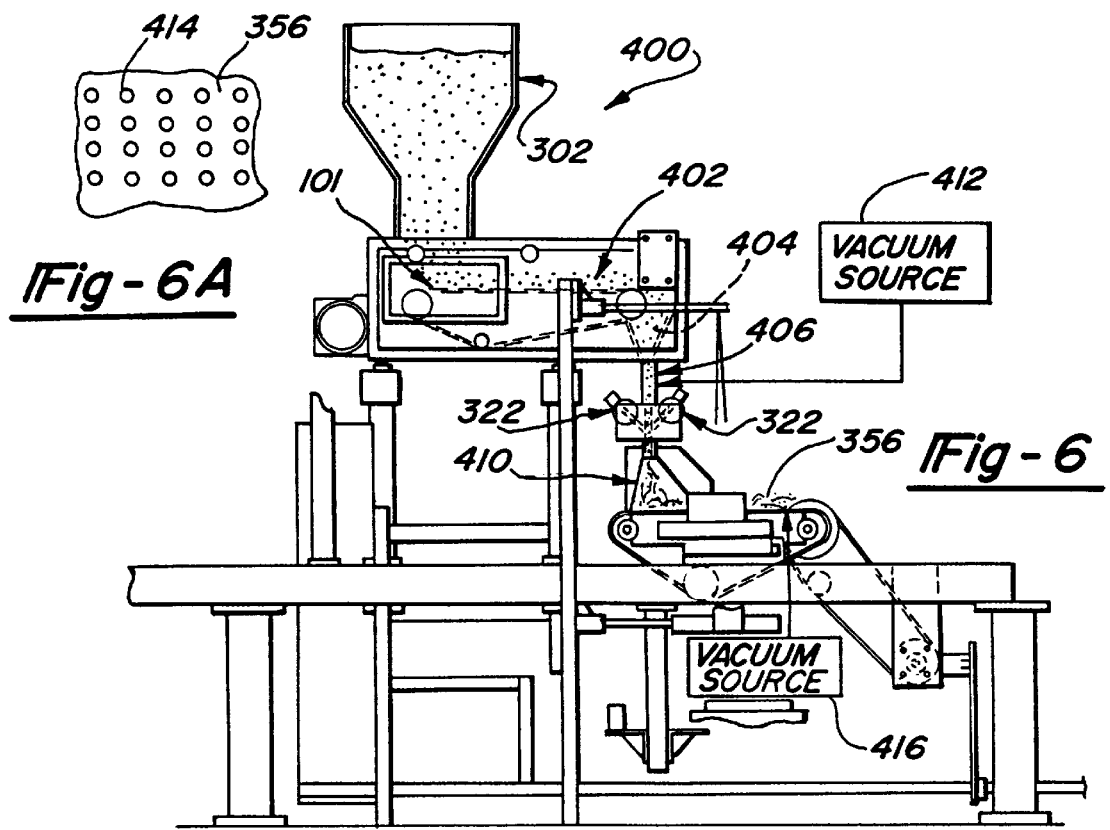
Fig-6A
Fig-6
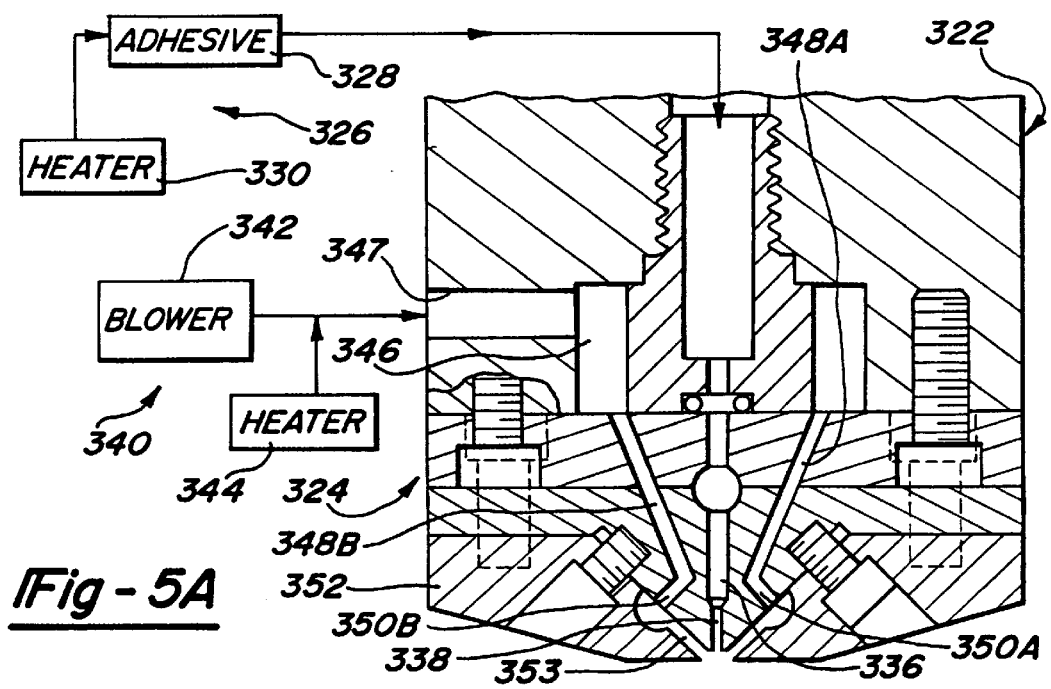
Fig-5A

METHOD AND APPARATUS FOR MAKING STRETCHABLE ABSORBENT ARTICLES

This is a continuation of U.S. patent application Ser. No. 08/346,653, filed Nov. 30, 1994, now U.S. Pat. No. 5,560,878.

CROSS REFERENCE TO RELATED APPLICATION

This application is one of two commonly owned, but related, applications filed on this date. The other related application is entitled "Stretchable Absorbent Article Core," and is hereby expressly incorporated by reference.

FIELD OF THE INVENTION

The present invention relates to stretchable absorbent articles having a first configuration, which are capable of elastically deforming in response to forces exerted by the wearer and are capable of returning to substantially to the first configuration. The present invention relates particularly to a method and apparatus for making stretchable absorbent articles, namely a stretchable absorbent core.

BACKGROUND OF THE INVENTION

Absorbent articles function to acquire, distribute and store urine and other body exudates. Examples of absorbent articles include, without limitation, diapers, sanitary napkins, panty liners, and incontinence articles. Nowadays, diapers are worn by infants and other persons, such as incontinent individuals.

Attention has been given to diaper technology from the standpoint of improving the functions of acquiring body waste materials from the body of the person wearing the diaper, isolating the acquired body waste material from the wearer's body, and protecting the clothing of such individual, and other surfaces that potentially could come into contact with such waste. In addition, attention has been devoted to improving diaper comfort, such as by reducing occurrences of events commonly associated with diaper wearer discomfort, e.g., without limitation, balling, slumping, cracking or tearing.

Other patents of potential background interest in diaper technology include U.S. Pat. Nos. 5,196,000 (Clear et al); 5,176,668 (Bernardin); 5,176,669 (Klemp); 5,176,670 (Roessler et al); 5,176,671 (Roessler et al); and 5,176,672 (Bruemmer et al); all of which are hereby expressly incorporated by reference herein. Also of possible interest is U.S. Pat. No. 5,197,959 (Buell) (incorporated by reference herein).

Most modern commercially available disposable diapers include an absorbent core structure that functions to absorb exudates discharged from the body of the wearer. Commonly, these cores include a conventional absorbent gelling material (which may be referred to herein as an "AGM" material) or a conventional superabsorbent material dispersed in a batt of cellulose fibers. Other conventional materials are discussed herein. While such core structures typically exhibit good absorbency characteristics, they tend to be limited in their ability to stretch under normal wear situations and, subsequently, to return substantially to their original configuration.

It is desired, therefore, and a need has developed for an absorbent core that is capable of stretching under normal usage situations, and conforming to the body shape of the wearer, while still exhibiting excellent absorbency characteristics, and while not slumping, balling, cracking, or tearing.

Recent developments in the absorbent article industry have included improved stretchable topsheets and backsheets. The ability to use such topsheets and backsheets, however, may be limited by the stretchability of any core element employed. Thus to improve the overall stretchability of absorbent articles made with the improved stretchable topsheets and backsheets, there has arisen a need for a stretchable core element.

A stretchable absorbent article, namely a sanitary napkin, is disclosed in co-pending commonly assigned PCT application No. WO 93/01785, entitled "Stretchable Absorbent Articles." An absorbent elastomeric wound dressing is disclosed in U.S. Pat. No. 4,957,795 (Riedel).

Additional background literature that may be of interest are U.S. Pat. Nos. 3,856,013 (Dulle); 4,229,548 (Sattlegger et al); 4,341,214 (Fries et al); 4,554,297 (Dabi); 4,584,324 (Bauman et al); 3,916,900 (Breyer et al); 4,394,930 (Korpman); 4,664,662 (Webster); 5,149,720 (DesMarais et al); 4,834,735 (Alemany); 4,610,678 (Weisman et al); 4,673,402 (Weisman et al); U.S. patent application Ser. No. 08/085,537, now U.S. Pat. No. 5,342,858; entitled "Elastomeric Adhesive Foam;" filed Jun. 30, 1993 in the names of Litchholt and Lodge; and U.S. patent application Ser. No. 08/085,237, now U.S. Pat. No. 5,389,168; entitled "Method of Making an Elastomeric Adhesive Foam and of Elasticizing Garments;" filed Jun. 30, 1993 in the names of Litchholt and Lodge.

SUMMARY OF THE INVENTION

The process, article and apparatus of the present invention are predicated upon the discovery of an improved stretchable article (e.g., a stretchable absorbent core, a stretchable absorbent core insert, combinations thereof, or stretchable components for articles such as, without limitation, sanitary napkins, panty liners, incontinence articles or the like) construction achievable through the dispersion of at least one absorbent material in a stretchable binder, which binder preferably includes an adhesive having at least one generally elastomeric component. The stretchable article exhibits excellent liquid absorbency characteristics and substantial elasticity in each of the x, y, and z dimensions, thereby permitting it to stretch or otherwise elastically deform in response to forces incurred during ordinary wear, and to return substantially to its original configuration after the forces are removed.

In one embodiment of the present invention, a disposable absorbent article, such as a diaper, is constructed to include a backsheet, a topsheet and a stretchable core between the backsheet and the topsheet. The backsheet preferably includes a relatively liquid impervious or non-porous plastic film that is substantially elastic in its entirety or has one or more substantially elastic portions. The topsheet is a generally liquid permeable or porous material that also is substantially elastic in its entirety, or has one or more substantially elastic portions.

According to the process of the present invention, a continuous process is employed that includes the steps of preparing the stretchable core and assembling the stretchable core into a diaper chassis, (i.e., between the backsheet and the topsheet). The stretchable core is prepared by contacting the absorbent material with the generally stretchable binder, and particularly by directing at least one stream of a melt-blown adhesive, which preferably includes an elastomeric component, into a collection or stream of the absorbent material. In one embodiment, the stream of absorbent material includes a stream of particulates of the absorbent material (also referred to as "particulated absorbent material"). Melt blowing of the adhesive produces a stream of heat-fusible discontinuous microfibers or filaments either of discrete or indeterminate lengths. The melt-blown stream of adhesive fibers or filaments is injected into the stream of absorbent material (i.e., so that it contacts the absorbent material), and under the forces from melt blowing, the fibers deform, collect and solidify to yield a generally bonded, randomly tangled mat-like network capable of containing the absorbent material. In one embodiment, the resulting stretchable core is assembled between a first stretchable, liquid permeable or porous web (preferably the topsheet) and a second stretchable, liquid impervious or non-porous web (preferably the backsheet). One or more suitable diaper configurations can be cut or otherwise prepared, and conventional diaper finishing techniques (e.g., fastener attachment) can be employed.

The apparatus for the manufacture of the diaper preferably includes a plurality of sequential processing stations. A first station is provided for forming a mat-like web of the stretchable core material by incorporating a predetermined amount of the absorbent material into a network of the stretchable binder material. In general, the first station is adapted to deliver and inject one or more streams of the binder material, which is preferably a meltblown adhesive having one or more elastic components, into a stream of the absorbent material. More specifically, the first station preferably includes means for conveying a metered quantity of the absorbent material at a predetermined velocity to the discharge end of a delivery chute for establishing a continuous particulated stream. Additionally, the first station further includes means for melt-blowing the stretchable binder material (e.g., a suitable hot melt adhesive having one or more elastomeric components) for producing a stream of molten microfibers or filaments that is subsequently injected into the absorbent material stream discharged from the delivery chute. Laydown and resolidification of the randomly entangled adhesive fibers or filaments interspersed with the absorbent material results in the formation of a mat-like web of the stretchable core material. As such, the first station further includes means for laying down the resulting network of the absorbent material as combined with fibrous meltblown adhesive on a continuous laydown conveyor. Optionally, the mat-like web of stretchable core material can be laid down or deposited on a continuous envelope material, preferably the porous stretchable topsheet for the diaper, to form a generally bonded assembly. A second station is located downstream from the first station for combining the mat-like web and topsheet with a second material web, preferably the backsheet for a diaper. Preferably, a third station includes one or more roller assemblies for delivering one or more finishing webs, such as elastics or fasteners, for lamination to the stretchable topsheet and backsheet.

Among the many advantages of the article, process and apparatus of the present invention are that absorbent cores having improved stretchability over other absorbent cores can be prepared efficiently and in a continuous manner. The absorbent core is capable of providing substantial absorbency, both when stretched and when not stretched, thereby taking advantage of the beneficial characteristics of the absorbent material, but not sacrificing substantial absorbency for stretchability. The core is thus capable of exhibiting improved liquid acquisition, liquid distribution and liquid storage characteristics and improved core structural integrity properties, as compared with various conventional absorbent cores. The core also exhibits substantial stretchability and resiliency; that is, it will permit deformation during use and is capable of returning substantially to its original configuration. Its deformability characteristics permit it, in service, to stretch and to conform generally to the wearer's body shape during normal movements. The absorbent core generally will not slump, ball or fracture during service, and exhibits generally high core integrity properties (including, but not limited to any or all of liquid acquisition, liquid distribution or liquid storage properties) in both its saturated and unsaturated states. The absorbent core also lends itself especially well to integration into a diaper preferably having a generally stretchable or garment-like chassis. Of course, the stretchable core is not intended to be limited to such applications. It may also be used simply as an adhesive bound core material in a conventional generally non-stretchable chassis. Absorbent articles according to the present invention (which are typically disposable and generally will be discarded after a single use) exhibit improved fit and comfort characteristics over conventional non-stretchable absorbent articles, without substantial sacrifice to absorbency characteristics.

BRIEF DESCRIPTION OF THE DRAWINGS

While the specification concludes with claims particularly pointing out and distinctly claiming the subject matter that is regarded as forming the present invention, it is believed that the invention will be better understood from the following description, which is taken in conjunction with the accompanying drawings in which like designations are used to designate substantially identical elements, and in which:

FIG. 5A is a partial sectional view of an exemplary extruder die or glue head used as the injection segment of the apparatus of FIG. 4;

FIG. 6 is a side elevation view of an apparatus for use in another embodiment for manufacturing a mat-like web for use as a stretchable core material;

FIG. 6A is a partial plan view of the conveyor including vacuum holes; and

DETAILED DESCRIPTION OF THE PREFERRED EMBODIMENT

Figure 1:
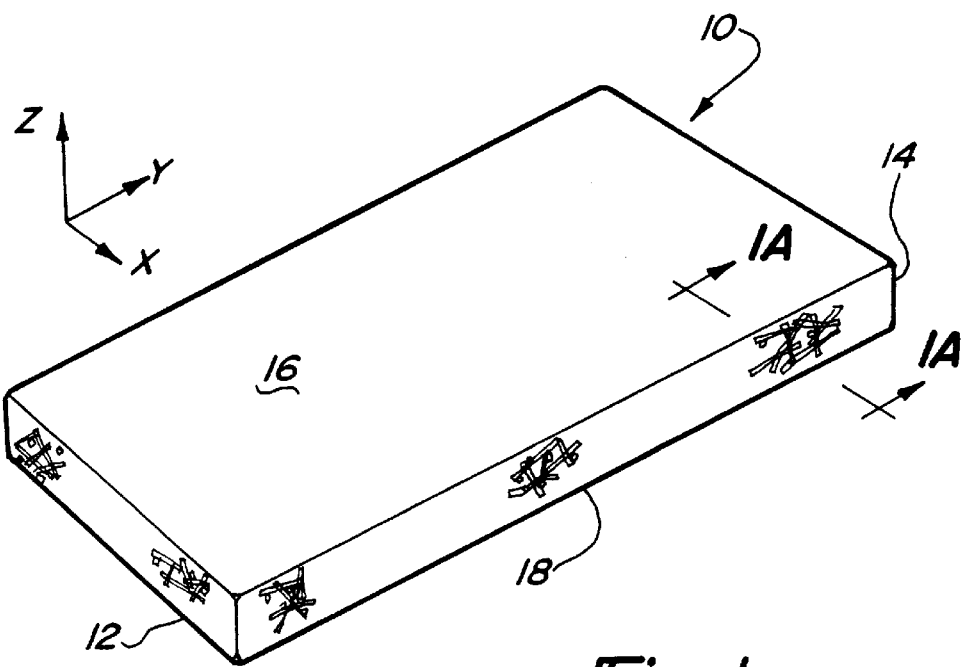
FIG. 1 depicts a core of the present invention.

As used herein, "absorbent article" refers to devices which absorb and contain body exudates, and, more specifically, refers to devices which are placed against or in proximity to the body of the wearer to absorb and contain the various exudates discharged from the body.

As used herein, the term "disposable" describes absorbent articles which are not intended to be laundered or otherwise restored or reused as an absorbent articles (i.e., they are intended to be discarded after a single use and, preferably, to be recycled, composted or otherwise disposed of in an environmentally compatible manner).

As used herein, "stretchable" refers to the ability of an article to stretch elastically or otherwise deform elastically in response to a force, such that it may be extensible in length (i.e., in the longitudinal direction) and/or width (i.e., in the transverse direction) and/or other directions, and to return substantially to its original unstretched configuration after the force is removed. More specifically, the term stretchable refers to: the ability of a 1 centimeter wide strip of the article to extend a minimum of 10% at 25 grams of force; a minimum of 100% at 40 grams of force; and a minimum of 200% at 60 grams of force. The article should sufficiently recover to at least 95% of its original dimension upon relaxion of force.

As used herein, "particulates", in the context of an absorbent material, refers to absorbent material in any form, shape, or size including but not limited to powders, pellets, grains, discrete length fibers, or the like.

As used herein, "liquid body exudate" refers to urine, runny bowel movements, or other matter excreted from the body. Unless otherwise gleaned from the context of discussion, references to a "liquid", a "fluid", or a "body fluid" herein shall include liquid body exudates.

As used herein, "absorbent" refers to the ability to absorb body exudates, such as urine.

As used herein, "liquid acquisition" refers to the act of receiving a liquid (e.g., a liquid body exudate) from the body of the wearer.

As used herein, "liquid distribution" refers to the act of transporting a liquid (e.g., a liquid body exudate) from a first location to a second location.

As used herein, "liquid storage" refers to the isolation and maintenance of a liquid (e.g., a liquid body exudates) within a generally predetermined region or volume.

As used herein, "binder" refers to a first material (e.g., a matrix material) for isolating and maintaining a second material within a generally predetermined region or volume.

As used herein, "diaper" encompasses not only a diaper of the type intended for use by infants or children, but absorbent articles intended for use by individuals of any age (e.g., incontinent individuals), including adults.

Structure of the Core

Preferred embodiments of the stretchable core of the present invention are shown in FIGS. 1, 1A, 1B, 2, 2A, 3 and 3A. In general the stretchable core preferably has a mat-like form, which includes a first predetermined amount of an absorbent material (discussed in greater detail herein) incorporated in a network of a stretchable binder material. The absorbent material (also referred to herein as an "absorbent") preferably is employed in the form of a predetermined amount of particulates. The binder material, which preferably is a meltblown adhesive having one or more elastic components, preferably is employed in fibrous form in a predetermined amount. The binder may serve one or more functions, including but not limited to contacting the absorbent material, bonding thereto, or bonding to itself to form a generally interconnected stretchable network for effectively isolating and maintaining the absorbent material within one or more predetermined regions or volumes of the network. Optionally, the core is encapsulated, partially or fully, in an elastic, stretchable, envelope-type structure.

Figure 2:
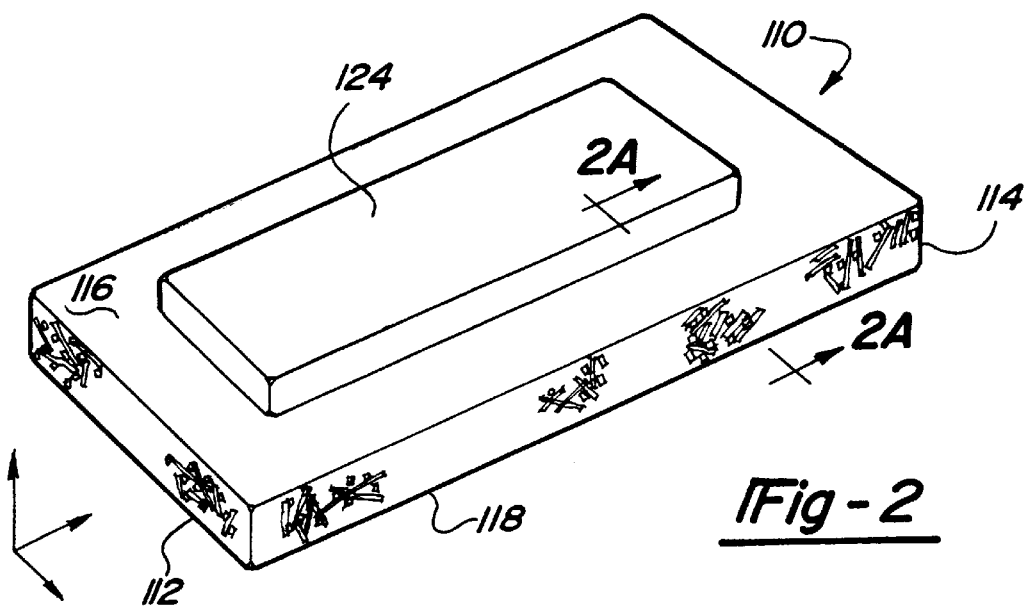
FIG. 2 depicts another core of the present invention.
Figure 3:
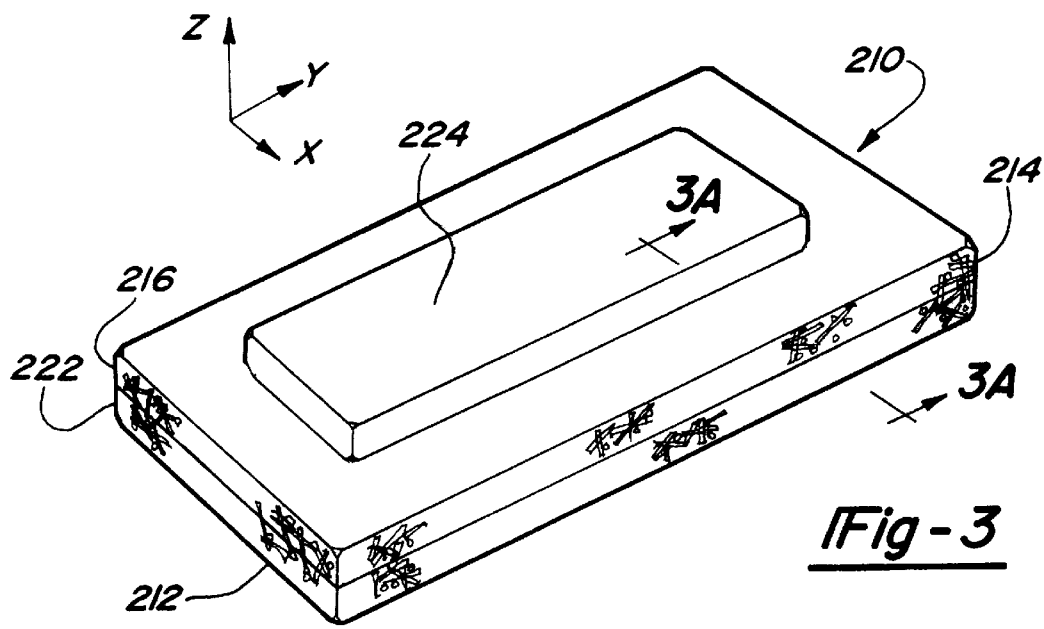
FIG. 3 depicts another core of the present invention.

The core preferably has one or more predetermined dimensions in each of the x, y, and z directions shown in FIGS. 1–3. The size and shape of the core is generally governed by practical considerations such as, without limitation, the size and shape of the ultimate absorbent article incorporating the core, and the desired amount of absorbency of the absorbent article. In one embodiment, the core, when dry, weighs in the range of about 8 g to about 18 g, and more preferably, about 10 g to about 16 g, and has a density ranging from about 0.07 g/cm$^3$ to about 0.16 g/cm$^3$, and more preferably about 0.09 g/cm$^3$ to about 0.14 g/cm$^3$ (as measured at a pressure of 1.4 kPa (0.2 psi)). The core, however, is preferably capable of absorbing (and thereafter storing) liquid body exudates in an amount at least up to about 1900% of its dry weight, more preferably about 2900% of its dry weight, and more preferably about 3400% to about 4400% of its dry weight. Of course, higher and lower weights, densities and absorbencies are possible as well.

In one embodiment, a representative section of such a core, having initial predetermined dimensions in each of the x, y and z directions, has an absorbent capacity and expansion properties such that it is capable of expanding substantially uniformly in each of the x, y and z directions to dimensions of two times to about three times, and preferably up to at least about five times the initial predetermined dimensions in a substantially fully saturated state (i.e., with liquid body exudates). It is also possible to vary the core so that it expands different amounts in different directions as will be apparent from the discussion herein. Further, the core may be designed with one or more densities selectively located at various positions within the core, for varying the properties or performance characteristics at various core locations.

A preferred core exhibits the properties as described in Table I set forth herein. The core also exhibits a bending modulus of about 25% to 50% of the sheet form as described in Table I. It should be noted that even though the properties of Table I are discussed in the context of a sheet form of the absorbent material, it is preferred that the overall core approximates those properties as well. That is, the process, article, and apparatus of the present invention seeks to yield an absorbent core that exhibits properties and characteristics that substantially approximate the advantageous properties and characteristics of the absorbent material by itself, its sheet form, while at the same time, exhibiting substantial stretchability.

The elastic, stretch and recovery properties preferably are such that the core, independent of any diaper structure into which it may be incorporated, can be stretched up to 100 to 200% of its original dimensions at a relatively low modulus extension force (e.g., 39–59 grams force based on a one centimeter wide sample) at about 100% elongation (peak), and recover to at least about 95% of the original dimensions while also being capable of absorbing liquid in an amount at least about 1900% of the overall weight of the core, and retaining the liquid. Alternatively, when the core is confined in an absorbent article structure, the modulus properties of the combined topsheet and backsheet materials of the absorbent article, in a preferred embodiment, will exceed and dominate those properties of the core, such that the forces required to extend the core are masked or hidden by the greater forces required to extend the topsheet and backsheet materials as a total absorbent article. Thus, the core conforms itself to the performance requirements of the absorbent article.

TABLE I

| FEATURE | EXAMPLE I FOAM | EXAMPLE II FOAM | Units |
|---|---|---|---|
| Structural Features | | | |
| Pore Volume | 36.8 | 31.8 | mL/g |
| Capillary Suction Specific Surface Area | 1.35 | 1.25 | m$^2$/g |
| Density | 0.029 | 0.032 | g/cm$^3$ |
| Average Cell Size | 40 | 37 | $\mu$ |
| Mechanical Features | | | |
| Strain Under 5.1 kPa Confining Pressure | 52% | 31% | % |
| Flexibility | >1 | >1 | bending cycles |
| % Recovery From 50% Compression | 95% | 94% | % |
| Fluid Handling Properties | | | |
| Absorbent capacity under a pressure of: | | | |
| 0.0 kPa (0.0 psi) | 35.9 | 31.5 | mL/g |
| 1.4 kPa (0.2 psi) | 34.0 | 29.1 | mL/g |
| 5.1 kPa (0.74 psi) | 23.4 | 25.1 | mL/g |
| 6.9 kPa (1.0 psi) | 13.0 | 14.8 | mL/g |
| % of 0.0 kPa capacity at 5.1 kPa | 65.2 | 79.7 | % |
| Vertical wicking time to 5 cm | 105 | 120 | sec |
| Absorbent capacity at a height up to: | | | |
| 1.3 cm (0.5 in) | 30.9 | 26.7 | mL/g |
| 3.8 cm (1.5 in) | 30.7 | 26.4 | mL/g |
| 6.4 cm (2.5 in) | 28.0 | 25.3 | mL/g |
| 8.9 cm (3.5 in) | 26.6 | 24.8 | mL/g |
| 11.4 cm (4.5 in) | 18.7 | 24.0 | mL/g |
| 14.0 cm (5.5 in) | 0.6 | 23.3 | mL/g |
| 16.5 cm (6.5 in) | 0 | 21.8 | mL/g |
| 19.1 cm (7.5 in) | 0 | 14.1 | mL/g |
| Adhesion Tension in 65 ± 5 dynes/cm Synthetic Urine | 30.7 | 37.8 | dynes/cmnn |

The core also preferably exhibits sufficient compressibility and resiliency to permit a finished absorbent article incorporating the core to be folded using conventional techniques (e.g., E-fold, C-fold, Bi-fold, tri-fold, or the like), stacked and packaged, and then to achieve its desired size, shape and performance characteristics when it is later used.

Figure 1A:
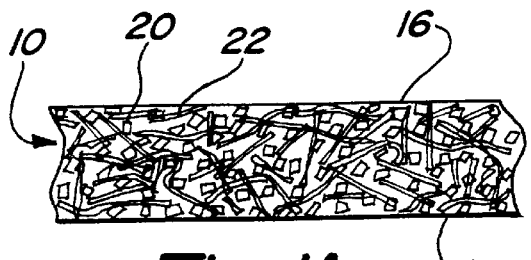
FIG. 1A depicts a section of the core of FIG. 1 taken along lines 1A—1A.
Figure 1B:
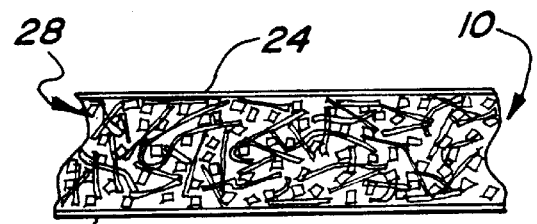
FIG. 1B depicts a section of a core disposed between a topsheet and a backsheet of a diaper.

Examples of suitable core shapes include rectangular, hour-glass, "T"-shaped, asymmetric, combinations thereof, or the like. In one embodiment, such as the core shown in FIGS. 1–3, the core is generally rectangular shaped. In FIGS. 1, 1A, and 1B, it is also monolithic, i.e., it has a single layer. In alternative embodiments, however, multiple core layers are contemplated, such as illustrated, without limitation in FIGS. 2, 2A, 3 and 3A.

FIG. 1 and FIG. 1A show a single layer or monolithic core 10 that is generally rectangular shaped. The core has a first end 12 and a second end 14. The core 10 has a first surface 16 and a second surface 18 spaced apart from the first surface 16 in the z direction of the core, thereby defining one or more thicknesses or calipers of the core in the z-direction of the core. When used in a diaper, for example, the caliper preferably ranges from about 2.5 mm to about 12.7 mm, more preferably about 3.8 mm to about 12.7 mm and still more preferably about 4.7 mm to about 6.4 mm. Another preferred caliper ranges from about 2.5 mm to about 5.0 mm. Larger or smaller calipers are possible, of course, as the skilled artisan will appreciate. For example, in an embodiment where a thinner caliper is desired, the caliper may range from about 1.25 mm to about 2.5 mm.

During normal wear, the first surface 16 is closer to the body of the wearer than the second surface 18. In a highly preferred embodiment, the caliper is as thin as possible (e.g., as thin as about 2.5 mm or thinner) without sacrificing a substantial amount of absorbency within the core 10.

The core 10 shown in FIGS. 1 and 1A is suitable for use in a diaper and has a generally rectangular shape with a width (i.e., in the x-direction) ranging from about 60 mm to about 150 mm, and more preferably about 100 mm to about 120 mm. Likewise, the core 10, also has a length (ie., in the y-direction) from the first end 12 to the second end 14, ranging from about 250 mm to about 500 mm, and more preferably about 350 mm, depending on such factors as the size of the diaper, the desired weight, or desired performance characteristics.

As indicated, the core size and shape may vary, and the present illustrative dimensions are not intended as limiting. In this regard, the drawings are not drawn to scale.

FIG. 1A shows a fragmentary cross-section of the core 10 of FIG. 1 illustrating a plurality of particulates 20 of the absorbent material interspersed with a plurality of fibers or continuous filaments 22 defining a mat-like network of the binder. In one preferred embodiment, each of the particulates 20 is preferably in contact with, or in close proximity to, a fiber 22. Moreover, in a preferred embodiment, the particulates 20 preferably are spaced a sufficient distance relative (in each of the x, y and z directions) to each other to permit them to expand, upon acquisition of liquid, and to come into contact with an adjacent particle, thereby permitting the acquired liquid to contact the adjacent particle and be transported to the adjacent particle. Preferably, the particulates 20 are spaced apart relative to each other by about 0.5 to about 2 particulate diameters or of sufficient distance to facilitate capillary forces to transport the liquid. The distance between the particulates 20 may also be chosen, where so desired, to restrict transporting of liquid between two or more adjacent particulates, such as by spacing adjacent particulates further apart, as will be appreciated from the present discussion.

The approximate specifications of one embodiment of the core having a configuration such as the one illustrated in FIG. 1 and FIG. 1A, are as follows in Table II. Unless otherwise noted, references to dimensions or quantities of the cores discussed herein are given on a dry basis (i.e., prior to contacting with a liquid).

TABLE II

| | |
|---|---|
| Core weight (g) | 10 g. |
| Overall core length (first end to second end) | 356 mm |
| Core width | 101 mm |
| Core thickness (measured under a pressure of ~1.4 kPa (0.2 psi) | 3 mm |
| Approximate number of particulates (in this configuration) | ~300 particles (~94–96 parts by weight) |
| Amount of binder | 0.4 g (~4–6 parts by weight) |
| Density of core (measured under a pressure of ~1.4 kPa (0.2 psi) | .09 g/cc |

Figure 2A:
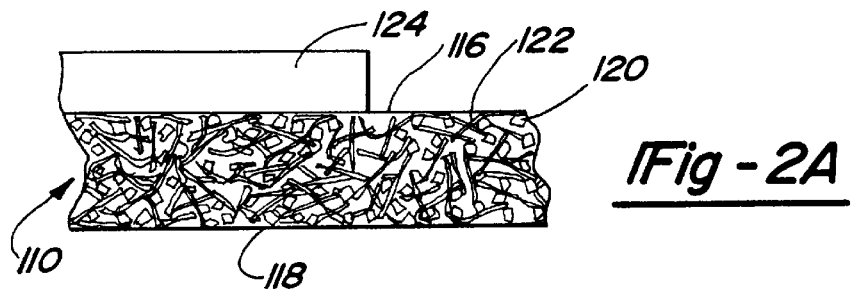
FIG. 2A depicts a section of the core of FIG. 2 taken along lines 2A—2A.

FIG. 2 shows an alternative core structure 110 to the core shown in FIG. 1. The core 110 of FIG. 2, has a first end 112, a second end 114, a first surface 116 and a second surface 118. FIG. 2A shows an enlarged fragmentary section of the core 110 that includes a plurality of particulates 120 of the absorbent material interspersed with a plurality of fibers or continuous filaments 122 defining a mat-like network of the binder The core of FIG. 2 and FIG. 2A is generally the same as the core of FIG. 1 and FIG. 1A, both in overall configuration and dimensions. However, the core of FIG. 2 and FIG. 2A differs from the core 10 of FIG. 1 and FIG. 1A in that it includes a patch 124. The patch 124 shown in FIGS. 2 and 2A is generally rectangular in shape. It is positioned on top of the core 110 of FIGS. 2 and 2A, and functions to improve the overall performance of the core structure by serving to perform one or more of the functions of liquid acquisition, liquid distribution or liquid storage. The patch may serve any other useful purpose including but not limited to the enhancement of core integrity properties, either with or without the patch imparting stretchability to the core. Accordingly, the patch 124 can be tailored specifically to achieve the desired objective.

The patch 124 may be adapted for employment in either a monolithic core, such as the present embodiment, or a multilayer core (as discussed herein). The patch 124 may be prepared in accordance with the method of the present invention (described in detail further herein), and may be a stretchable absorbent structure in accordance with the structure of the core of the present invention. Alternatively, it may be prepared using conventional techniques for making absorbent core structures, and may incorporate one or more conventional absorbent (and potentially non-stretchable) materials.

By way of example, the patch 124 may include known polymeric gelling agents, such as an absorbent gelling material (referred to in the art as an "AGM" material) or superabsorbent materials, in a batt of cellulose fibers (which may be referred to herein as "straight fibers"), or chemically modified cross-linked cellulose fibers (which may also be referred to herein as "curly fibers"). Suitable chemically modified cross-linked cellulose fibers are described in U.S. Pat. No. 4,888,093 (Cook, et al); U.S. Pat. No. 4,822,543 (Dean, et al); U.S. Pat. No. 4,898,642 (Moore, et al); U.S. Pat. No. 4,935,022 (Lash, et al); U.S. Pat. No. 5,137,537 (Herron, et al); and U.S. Pat. No. 5,183,707 (Herron, et al). All of the foregoing are hereby expressly incorporated by reference herein. Suitable polymeric gelling agents include known materials that, upon contact with a liquid, form hydrogels. They are generally substantially water-insoluble, slightly cross-linked, partially neutralized, hydrogel-forming polymer materials. See, e.g., U.S. Pat. No. Re. 32,649 (Brandt, et al), incorporated by reference. Another example of a suitable material for use in a patch is polyethylene terephthalate fibers.

Patches such as the present patch 124 may be pre-formed and then provided at the site of core manufacture e.g., via a delivery mechanism such as a drum for rolling it onto a core that is laid down. Alternatively, and preferably, the patch 124 may be placed onto the stretchable absorbent core 110 by conventional cut and slip techniques. In yet another embodiment, the core may be made as part of the core manufacture process, at a separate location from the site of manufacture of the stretchable mat-like network of the core structure, either upstream or downstream from the site. The patch and the stretchable mat-like network of the core structure may then be mated in accordance with any suitable technique, such as the above techniques (e.g., drum rolling, or cut and slip techniques).

In the embodiment of FIG. 2 and FIG. 2A, the patch 124 is generally a rectangular prism shape, preferably having a caliper or thickness (in the z-direction) of about 0.50 mm to about 0.80 mm, and preferably about 0.65 mm; a width (in the x-direction) of about 90 mm to about 100 mm, and preferably about 95 mm; and a length (in the y-direction) of about 240 mm to about 260 mm, and preferably about 250 mm. These dimensions also may vary higher than, lower than, or within the above ranges depending upon such factors as the functional objective of the patch, the size and shape of the core, the materials used, and the like. Preferably the length and width of the patch is less than the respective length and width of the overall core.

Figure 3A:
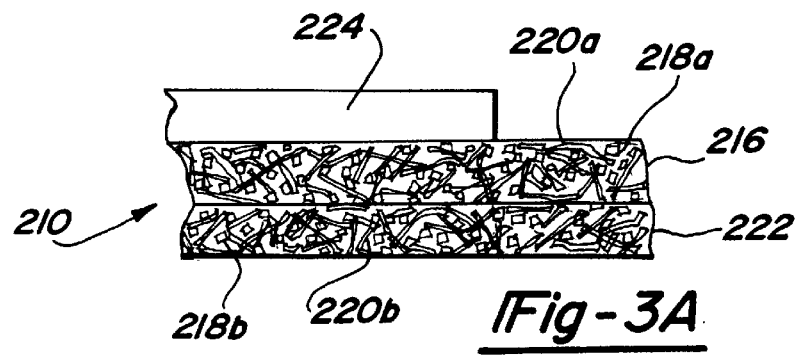
FIG. 3A depicts a section of the core of FIG. 3 taken along line 3A—3A.

FIG. 3 and FIG. 3A illustrate yet another embodiment of a core of the present invention. The core 210 of FIG. 3, has a first end 212, and a second end 214. The core 210 of FIGS. 3 and 3A differs from the core 10 of FIG. 1 and FIG. 1A in that it includes a first layer 216 having a plurality of first particulates 218$a$ of a first absorbent material and first fibers 220$a$. A second layer 222 is disposed on at least a portion of the first layer 216, and has a plurality of second particulates 218$b$ of a second absorbent material, and second fibers 220$b$. The core 210 also includes a patch 224 disposed over at least a portion of the first layer 216.

By way of illustration, without limitation, the layers of the embodiment of FIG. 3 and FIG. 3A each perform a different function. The patch 224 preferably functions as an acquisition layer and, in use, it will be closest to the body of the wearer. The patch 224 may be any suitable patch, such as any of those described above with respect to the embodiment of FIG. 2 and FIG. 2A.

The first fibers 220$a$ preferably are part of a first fibrous network that includes a stretchable binder, as described more fully herein. The first layer 216 preferably functions as a distribution or storage media. This is accomplished by the use of the plurality of first particulates 218$a$ in the first fibrous network. The absorbent material of the first particulates 218$a$ is preferably an opencelled foam with an average cell size of about 5 to about 100 microns, and has a relatively lower capillary suction specific surface area (e.g., toward the lower end of the range of about 0.5 to about 5.0 m$^2$/g), as compared with the absorbent material of the second particulates 218$b$. The second layer 222 employs the second particulates 218$b$, which preferably function as a storage material and is an absorbent material that is an open-celled foam with an average cell size of about 5 to about 100 microns, and a relatively higher capillary suction specific surface area (e.g., toward the higher end of the range of about 0.5 to about 5.0 m$^2$/g) than the absorbent material of the particulates 218$a$ of the first layer.

The second fibers 220$b$ preferably are part of a second fibrous network that, apart from the different absorbent material it incorporates from that in the first fibrous network (as discussed above) is substantially the same as the first fibrous network. It will be recognized that the embodiments of FIGS. 1–3 are illustrated with particulates of absorbent material. However, other forms of absorbent material are useful as well in those embodiments.

By way of illustration, without limitation, for the core of FIG. 3A, the thicknesses or calipers of the first layer 216 and the second layer 222 are about the same, and are preferably about 1.35 mm each. The first layer 216 includes particulates 218$a$ that are generally random geometric shapes, and have a size ranging from about 0.25 mm to about 6.40 mm, and more preferably about 0.50 mm to about 1.80 mm. As can be appreciated by skilled artisans, larger or smaller particulate sizes are possible as well. The first particulates 218$a$ are generally uniformly dispersed within the first layer 216 in a manner as described previously.

The second layer 222 includes the second absorbent material in the form of second particulates 218b, which are generally random geometric shapes, and preferably have a size ranging from about 0.10 mm to about 6.40 mm, and more preferably about 0.50 mm to about 1.80 mm. The second particulates 218b are generally uniformly dispersed within the second layer 222.

To achieve the above-described stricture, the respective layers and the patch are made separately from each other, and are brought together at a predetermined downstream location. In addition to the foregoing, differences between the layers, to achieve each of their respective functions, may be accomplished by varying one or more factors such as thickness of the layer, composition or type of the absorbent material, the size, shape or distribution of the absorbent material or the like.

In another embodiment it is possible to achieve a similar result as with the above embodiment (which is characterized as having discrete layers), by admixing and profiling the first absorbent material with the second absorbent material, and then incorporating the admixture of the two different absorbent materials into a monolithic or multilayer core structure. In this manner, precise tailoring of properties may be accomplished in each of the x, y, and z directions, such as, without limitation, by varying the amounts of the absorbent materials per unit volume at various locations throughout the core (i.e., by profiling). The different respective absorbent materials are pre-mixed or blended in a vat hopper or are delivered as separate material streams for combination and mixing at the adhesive binder addition point, the principles of which will be discussed further herein.

In another embodiment (not shown), the core is encapsulated in a generally liquid permeable, porous, stretchable, envelope layer (not shown) or envelope over some or all of the exterior surface of the core. Examples of suitable materials for use as an envelope layer include, without limitation, an elasticized, low gauge, hydroformed film, elasticized meltblown non-woven material, or a creped cellulose tissue.

The Binder Used in the Core

The binder employed in the core of the present invention preferably is a suitable meltblown adhesive. The use of the term "adhesive" herein is not intended as limiting, nor is it intended to exclude other suitable materials that perform the function of the adhesive described herein, regardless of their designation or form of supply. The skilled artisan will appreciate that any of a number of melt-blown adhesives or equivalent materials may be employed.

While a wide range of adhesive amounts may be employed in accordance with the present invention, the preferred amounts are about 2% by weight to about 10% by weight, and more preferably, 4% by weight to about 6% by weight of the overall core, in its dry state. The balance is preferably absorbent material. In a preferred embodiment, accordingly, the adhesive is present from about 2 to 10 parts by weight adhesive for every about 90 to 98 parts by weight absorbent material. More preferably, the adhesive is present from about 4 to 6 parts by weight adhesive for every about 94 to about 96 parts by weight absorbent material. This applies as well to each of the respective layers in a multi-layer core, such as described previously.

In one embodiment, the adhesive is capable of forming a melt when it is heated to a temperature as low as about 150° C. to about 175° C. A softening point, as measured by ASTM Ring and Ball Test Method E-28-51T, of the adhesive at least as low as about 110° C. is desirable. The specific gravity of the adhesive preferably ranges from about 0.95 to about 1.01 (where the specific gravity of water is 1.0). In other embodiments, the specific gravity may be higher or lower. In a preferred embodiment, the viscosity characteristics (measurable using a Brookfield Thermosel in accordance with ASTM method D 3236-73) of the adhesive is as detailed in Table III:

TABLE III

| Temperature | Viscosity (cps) |
|---|---|
| (135° C.) 275° F. | 335,000 |
| (149° C.) 300° F. | 90,000 |
| (163° C.) 300° F. | 33,000 |
| (177° C.) 350° F. | 17,000 |

An example of one particularly preferred adhesive is available from Findley Adhesive Company of Elm Grove, Wis. under the designation H2343-01. Other examples are described in pending U.S. patent application Ser. No. 07/911,953, filed Jul. 10, 1992, now abandoned, hereby incorporated by reference, which is assigned to Findley Adhesives. Other examples of suitable adhesives include, without limitation, the 2300 Series of adhesives by Findley Adhesives, the 2400 Series of adhesives by Findley Adhesives, and HL1258 available from Fuller Co. of St. Paul, Minn.

Figure 7A:
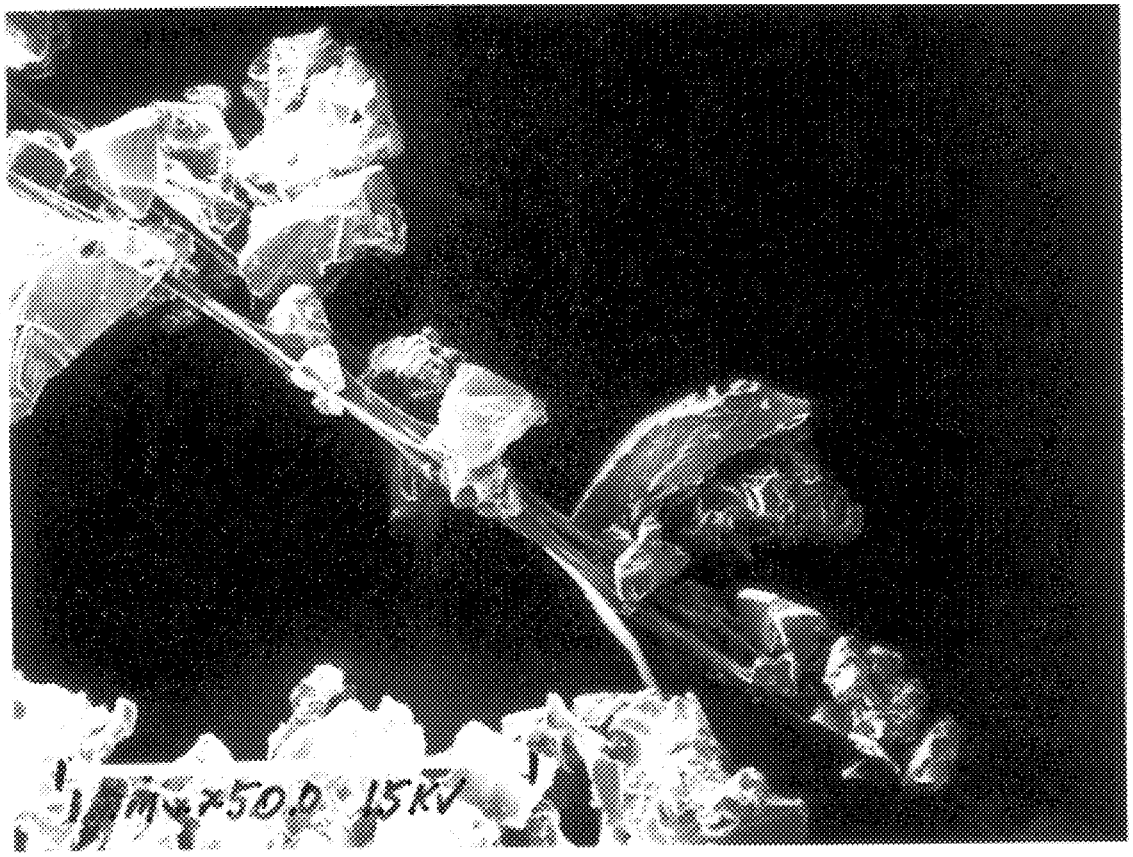
FIGS. 7A, 7B and 7C are micrographs depicting an example of a stretchable core article containing AGM particles entangled within a mat of meltblown glue fibers.
Figure 7B:
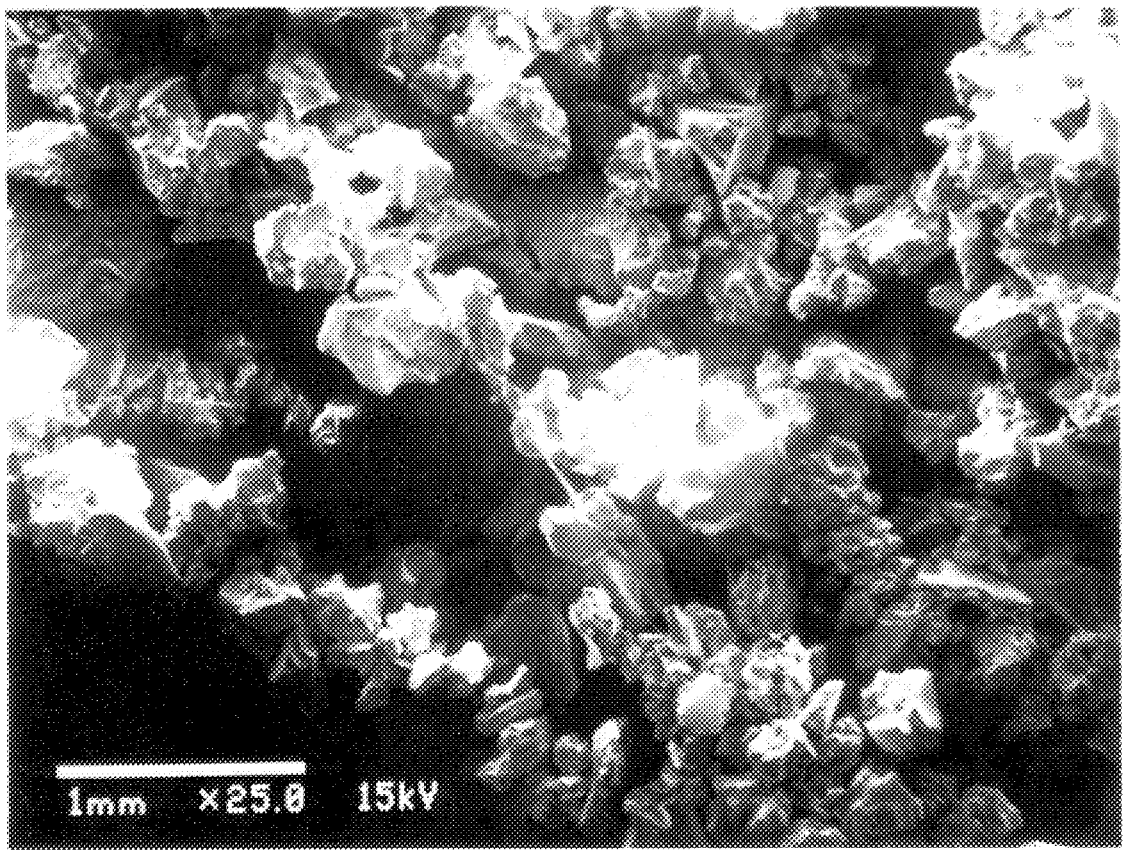
Figure 7C:
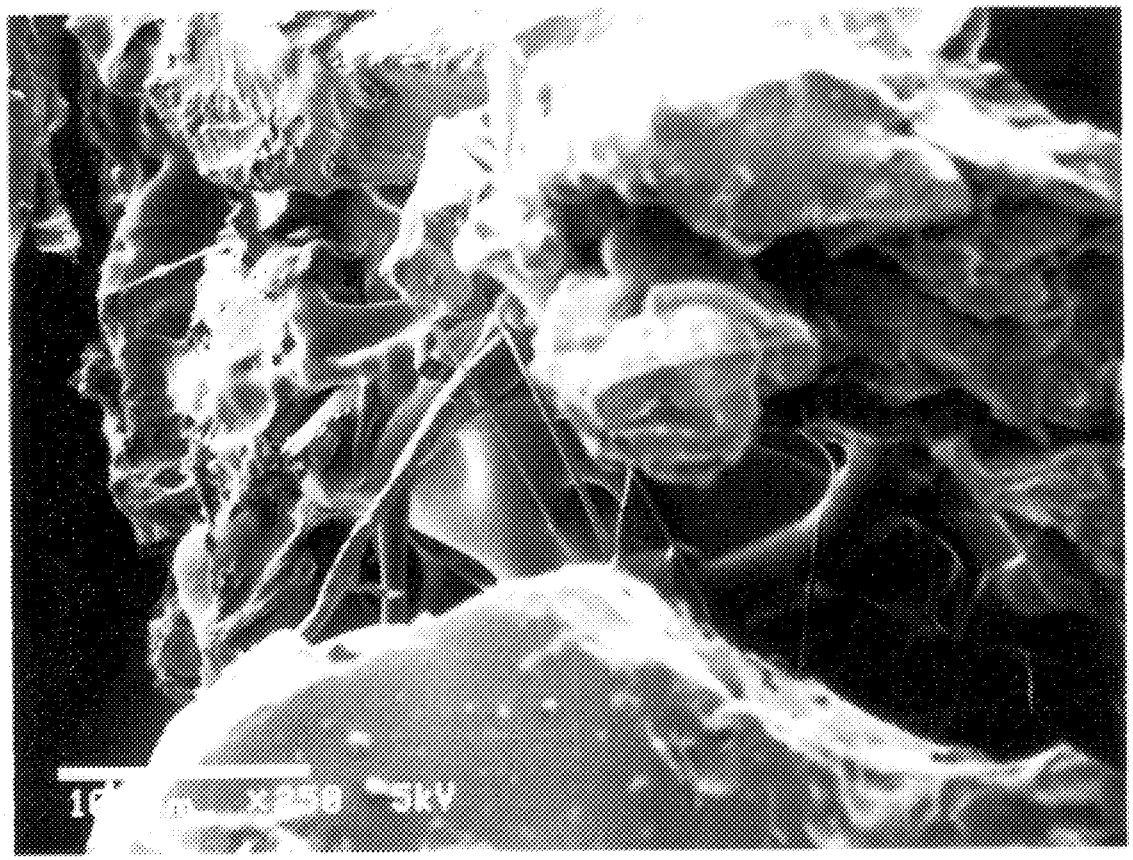

As will be discussed further herein, the melt-blown adhesive is preferably brought into contact with the absorbent material by melt blowing the adhesive through a melt blowing system, including an apparatus for dispensing the adhesive (e.g. a "glue head"), which preferably includes at least one nozzle through which the adhesive is blown. As a result, one or more streams of the meltblown adhesive can be blown and contacted with the absorbent material with the process aid of a heated gas, preferably air, until the desired core structure is completed. After being blown, the adhesive is generally fibrous, and includes a single fiber or filament or a plurality of fibers or filaments. Thus, the resulting series of fibers are typically continuous filaments or have one or more discrete lengths, and will have a fiber diameter in the range of about 5 microns to about 120 microns, and still more preferably, about 7 microns to about 30 microns. The resulting binder will preferably include a plurality of such fibers distributed in sufficient amount to achieve the desired core caliper and shape as was discussed previously. The fibers may be distributed generally in a random manner, in a non-woven manner, or in a generally sine-wave like manner to achieve a mat-like network or web. A typical example of a filament of adhesive employed in the stretchable binder is depicted in FIGS. 7A, 7B and 7C. Preferably, the overall absorbent core potentially will derive substantially all of its stretchability characteristics from the adhesive in the binder.

Accordingly, in a particularly preferred embodiment, the melt-blown adhesive is a hot-melt, pressure-sensitive tape of adhesive, thereby permitting it to bond, with or without another adhesive, to the absorbent material, to itself (and to other layers in a multilayer structure), and also (as desired) to either the topsheet or backsheet of an ultimate absorbent article structure. In a particularly preferred embodiment, the meltblown adhesive includes, in a predetermined amount, a stretchable (e.g., elastomeric) component, preferably an A-B-A type block co-polymer, where the A refers to end groups of a styrene-containing material (or the equivalent), and B is a generally elastomeric material. More particularly, the preferred adhesive preferably includes:

(a) an elastomeric, hot melt, pressure sensitive adhesive composition with
  (i) about 15% to about 60%, by weight of the overall adhesive composition, of an A-B-A block copolymer, where the A block is selected from the group consisting of styrene, alphamethyl styrene, and vinyl toluene and the B block is selected from the group consisting of butadiene and isoprene;
  (ii) about 30% to about 70% by weight of the overall adhesive composition, of an aromatic modified hydrocarbon resin which associates with both the midblock and the end blocks of the A-B-A block copolymer; and
  (iii) 0 to about 30%, by weight of the overall adhesive composition, of a processing oil.

The foregoing preferably are selected to result in an adhesive having a melt temperature of between about 138° C. to about 260° C., a viscosity of less than about 200,000 cps at about 325° F. (163° C.), an application viscosity (i.e., a viscosity at about the time it is meltblown of less than about 50,000 cps) and an elastomeric retention (as defined further herein) of greater than about 75%. Further, preferably the adhesive has a density of at least about 0.8 g/cm$^3$, but no greater than about 1.2 g/cm$^3$. Since the adhesive is to be meltblown, the adhesive preferably is capable of resulting in a forming distance (i.e., the distance between a discharge nozzle orifice and a substrate to which the material is applied) of from about 12.7 mm to about 127 mm with a resulting drop of temperature along the length of formed filaments of about 10° C. for each approximately 25.4 mm of filament forming distance.

The adhesive also preferably exhibits good forming edge definition (i.e., the consistency of adhesive pattern width during filament formation), preferably an edge definition variation within about 1.6 mm of the desired pattern width, when forming within a preferred forming distance of about 12.7 mm to about 25.4 mm, and up to about 4.8 mm edge definition variation for forming distances of about 100 mm.

Examples of preferred adhesives include those having a component selected from the group consisting of styrene-butadiene-styrene (S-B-S), styreneisoprene-styrene (S-I-S), or mixtures thereof. Optionally, the adhesive may be or include styrene-ethyl/butadiene-styrene (S-E/B-S); i.e., the B component of the A-B-A block copolymer is ethyl/butadiene, employed in proportions to achieve results indicated above.

The S-I-S and S-B-S copolymers are particularly preferred in the present formulations. The S-I-S or S-B-S block copolymer component of the adhesive may be of two specific classes, an unvulcanized elastomeric block copolymer, or a teleblock copolymer.

(1) An unvulcanized elastomeric block copolymer wherein the respective monomeric moieties are arranged in an alternating sequence having the general configuration S-I-S or S-B-S. In this first class, "S" is a generally non-elastomeric block derived from styrene, and "I" or "B" is an elastomeric polymeric block derived from isoprene or butadiene, respectively. In the preferred embodiment, the total concentration of styrene in the block copolymer may vary in a wide range of about 15%, to about 50% by weight of the overall copolymer composition. The block copolymers preferably are substantially 100% fully coupled, with lower coupling amounts being less preferred.

Suitable S-I-S block copolymers for use herein are commercially available from the Dexco Chemical Company of Houston, Tex. under the product or trade designations Vector 4211, Vector 4411, and Vector 4111, respectively. In this regard, Vector 4211 and 4411 are believed to have respective styrene contents of about 29% and 44% by weight of the overall copolymer. Further, a suitable S-I-S block copolymer may be provided by the Shell Chemical Company of Houston, Tex. under the trade designation RP6407. This copolymer and Vector 4111, which is provided by The Dexco Chemical Company, each are believed to have a styrene content of about 17% by weight of the overall copolymer composition.

(2) A teleblock copolymer including molecules having at least three branches which radially branch out from a central hub, each of the branches having polystyrene terminal blocks and an isoprene or butadiene segment in the center. This type of block copolymer may also be described as having a branched polymerized isoprene or butadiene midblock with a polystyrene terminal block at the end of each branch. The total concentration of the styrene monomer would similarly range from about 15% to 50%, by weight of the overall copolymer composition. This second class of copolymers preferably is substantially fully coupled.

It will also be recognized that mixtures of the above-identified block copolymers may also be employed.

Another example of a suitable material for use in the present adhesive is available from the Firestone Chemical Co. of Akron, Ohio under the trade designation of "Stereon."

In a preferred embodiment the concentration of diblock (S-I) present in the block copolymer mixture (S-I-S) (that is, an S-I-S block copolymer that is not substantially fully coupled) is kept to a minimum. It is believed that a relationship may exist between elastomeric retention in the compositions at a given interval or time, and the coupling efficiency of the S-I-S block copolymer employed. It is further believed that by decreasing the amount of diblock present in a composition the elastomeric retention of the composition at the same given time interval can be increased. Additionally, it is believed that decreasing the amount of diblock present in the S-I-S block copolymer additionally increases the tensile strength of the same composition.

In another embodiment S-I-S block copolymers are employed having the characteristics noted above, but further having a styrene concentration in the range of about 25–50% by weight of the overall copolymer composition. Compositions in this range are believed to display particularly desirable viscosities when compared with compounds manufactured from related A-B-A copolymers which have less than about 25% styrene, by weight, of the overall copolymer.

The aromatic modified hydrocarbon resin employed in the adhesive, which associates with both the midblock and the end blocks of the styrene-isoprene-styrene block copolymer, is commercially available from the Exxon Chemical Company of Houston, Tex. under the trade designation "ECR 165A and ECR 165C," respectively. Additionally, suitable styrenated terpenes, such as those materials which are marketed under the trade designation "Zonatac 105 lite" by the Arizona Chemical Company of Port St. Joe, Fla. may be substituted in place of the aromatic modified hydrocarbon resins noted above. The styrenated terpenes are examples falling within the above phrase "aromatic modified hydrocarbon resin."

The present compositions have a desirable viscosity, from a manufacturing standpoint, and further are believed have an elastomeric retention greater than about 75%. Additionally, the present compositions have a relatively fast speed of recovery following elongation.

Various plasticizing or processing oils may also be present in the adhesive compositions of the present invention in amounts ranging from about 0% to about 30%, by weight of the overall adhesive composition, in order to aid in providing viscosity control, and further to operate as a diluent. Paraffinic or napthenic white processing oils. A commercially available white processing oil is sold by the Witco Chemical Company of Marshall, Tex. as "Witco Plastics Oil 380." Additionally, a suitable oil may be purchased under the trade designation "Kaydol."

Suitable antioxidants/stabilizers may also be used in suitable amounts in the adhesive composition to help protect the A-B-A block copolymer, and thereby the total adhesive composition, from potentially deleterious thermal and oxidative effects which may take place during the manufacture and application of adhesive compositions employing the copolymer, as well as in the ordinary use of the final core. Such degradation, if it occurs, usually manifests itself by the deterioration of the adhesive composition in appearance, physical properties and performance. Without limitation, examples of useful stabilizers include one or more of high molecular weight hindered phenols and multi-functional phenols, such as sulfur and phosphorous-containing phenols. Examples of suitable hindered phenols include those that may be purchased commercially under the trade designation "Irganox 1010" from the Ciba-Geigy Company of Greensboro, N.C. Other examples include, without limitation, "Cyanox LTDP", which is manufactured by American Cyana mid of Wayne, N.J. and "Mark 273," which is manufactured by the Witco Chemical Company. It is believed that the performance of these stabilizers may be further enhanced by employing in conjunction therewith; (1) synergists such as, for example, thiodipropionate esters and phosphites; and (2) chelating agents and metal deactivators as, for example, ethylenediaminetetraacetic acid, salts thereof and disalicylapropylenediimine.

The composition of the present invention may be formulated using any of the techniques known in the art. A representative example of such a technique involves placing all of the oil and stabilizer substances in a jacketed mixing kettle, and preferably in a jacketed heavy duty mixer which is equipped with rotors and is sold by Baker-Perkins of Fort Collins, Colo. Thereafter, the temperature of this mixture is raised to about 121° C. to about 177° C. The precise temperature to be used in this step will depend on the melting point of the particular ingredients. When the initial mixture noted above has been heated, the mixture is blanketed in $CO_2$ at a relatively slow flow rate and the resins described above are slowly added. When the resins are melted, and at the desired temperature, the S-I-S block copolymer is added to the mixture. The resultant adhesive composition mixture is agitated thereafter until the S-I-S block copolymer is completely dissolved. A vacuum is then applied to remove substantially all entrapped air.

Specific illustrative examples, without limitation, of compositions employing an S-I-S block copolymer are described in the following.

Adhesive 1

45 parts, by weight, of an S-I-S block copolymer (Vector 4111; Dexco Chemical Company 17% styrene);

40 parts, by weight, of an aromatic modified hydrocarbon resin ("ECR 165A"; Exxon Chemical Company);

15 parts, by weight, of a paraffinic/napthenic white processing oil ("Kaydol"; Witco Chemical Company);

0.5 parts, by weight, of a stabilizing antioxidant ("Mark 273"; Witco Chemical Company);

0.25 parts, by weight, of a hindered phenol antioxidant ("Irganox 1010"; Ciba-Geigy Corporation); and 0.25 parts, by weight, of a DLTDP antioxidant synergist ("Cyanox LTDP"; American Cyanamid Corporation).

Adhesive 2

45 parts, by weight, of an S-I-S block copolymer ("Vector 4211"; Dexco Chemical Company, 29% styrene);

40 parts, by weight, of an aromatic modified hydrocarbon resin ("ECR 165C"; Exxon Chemical Co.);

15 parts, by weight, of a paraffinic/napthenic processing oil ("Kaydol"; Witco Chemical Company);

0.25 parts, by weight, of a hindered phenol antioxidant ("Irganox 1010"; Ciba Geigy Corporation);

0.25 parts, by weight, DLTDP; and ("Cyanox LTDP" American Cyanamid Corporation); and 0.50 parts, by weight, of a compatible stabilizer. ("Mark 273"; Witco Chemical Company).

Adhesive 3

45 parts, by weight, of an S-I-S block copolymer ("Vector 4411"; Dexco Chemical Company; 44% styrene);

40 parts, by weight, of an aromatic modified hydrocarbon resin ("Zonatac 105 Lite"; Arizona Chemical Company);

15 parts, by weight, of a processing oil ("Kaydol"; Witco Chemical Company);

0.25 parts, by weight, of a hindered phenol antioxidant ("Irganox 1010"; Ciba-Geigy Corporation);

0.25 parts, by weight, of DLTDP ("Cyanox LTDP"; American Cyanamid Corporation); and 0.50 parts, by weight, of a compatible stabilizer ("Mark 273"; Witco Chemical Company).

Adhesive 4

45 parts, by weight, of an S-I-S block copolymer ("Vector 4211"; Dexco Chemical Company; 29% Styrene);

40 parts, by weight, of an aromatic modified hydrocarbon resin ("Zonatac 105 Lite"; Arizona Chemical Company);

15 parts, by weight, of a paraffinic/napthenic processing oil ("Kaydol"; Witco Chemical Company);

0.25 parts, by weight, of a hindered phenol antioxidant ("Irganox 1010"; Ciba Geigy Corporation); and 0.25 parts, by weight, of DLTDP ("Cyanox LTDP; American Cyanamid Corporation).

Adhesive 5

45 parts, by weight, of an S-I-S block copolymer ("Vector 4211"; Dexco Chemical Company; 29% Styrene);

40 parts, by weight, of an aromatic modified hydrocarbon resin ("ECR165C"; Exxon Chemical Company);

15 parts, by weight, of a paraffinic/napthenic processing oil (Witco Plastics Oil 380; Witco Chemical Company);

0.25 parts, by weight, of a hindered phenol antioxidant ("Irganox 1010"; Ciba-Geigy Corporation);

0.25 parts, by weight, of DLTDP ("Cyanox LTDP"; American Cyanamic Corporation); and 0.50 parts, by weight, of a compatible stabilizer (Mark 273; Witco Chemical Company).

Discussion of Properties of Adhesives 1–5

Elastomeric Retention of the Adhesive measures the force of recovery exerted or exhibited by a sample of the composition during a predetermined interval of time following elongation. To measure elastomeric retention, samples of the composition can be coated on a LH1 coater sold by Acumeter of St. Paul, Minn. (a division of May Coating Technologies). The coating preferably is about 5 mils thick and approximately 1.5 inches (38.1 mm) wide. A carrier substrate is used for the coating and includes a double-sided release paper. Samples are rewound onto themselves. Following a period of storage for 24 hours, the samples are cut, in the machine direction, to become a size of about 1 inch (25.4 mm) and to remove flaws in the samples potentially existing along their edges. Samples are then cut to an appropriate size and placed in a Series IX Tensile Tester sold by Instron Co. of Canton, Mass. Each sample to be tested is elongated or pulled to a distance which represents an elongation equal to 40% of its unstressed length, and in a second series of tests, 80% of its unstressed length, at a rate of 20 inches per minute (50.8 cm/min.). The samples are held at these distances for a period of thirty (30) seconds. Following this first holding period, the force of elongation is removed, thereby permitting the individual samples to return or retract to their original length. The period of rest is about 1 minute. Following the period of rest, the force of elongation is again applied for a second holding period to extend the sample to the same distance at about the same rate of speed, (50.8 cm/min.). Measurements of the elastomeric recovery force of the samples are taken at the beginning of the test; at the beginning of the first holding period; at the end of the second holding period; and at the end of the second cycle. The percent elastomeric retention is calculated by generating a fraction which has, as its numerator, the force exerted by the sample at the end of the second holding period; and as its denominator, the force exerted at the beginning of the first holding period. This fraction is then multiplied by 100 to provide a product which equals the percent of elastomeric retention.

The following approximate results are believed possible:

1. Adhesive 1, when employing 100% coupled S-I-S copolymer—84.19% retention;
2. Adhesive 2, when employing, 100% coupled S-I-S copolymer—89.7% retention;
3. Adhesive 3, when employing 100% coupled S-I-S copolymer—84.7% retention;
4. Adhesive 4, when employing 100% coupled S-I-S copolymer—93.3% retention; and
5. Adhesive 5, when employing 100% coupled S-I-S copolymer—90.5% retention.

Viscosity of the Adhesive is measured in centipoise (cps) using a Thermosel sold by Brookfield of Stoughton, Mass. in accordance with ASTM Method D3236-73. The same samples are believed to exhibit the following approximate viscosity characteristics at about 325° F. (163° C.):

1. Adhesive 1: 34,000 cps;
2. Adhesive 2: 23,300 cps;
3. Adhesive 3: 11,125 cps;
4. Adhesive 4: 21,000 cps; and
5. Adhesive 5: 25,250 cps.

Tensile Strength of the Adhesive is measured using samples in accordance with the above, but the amount of S-I-S coupling is varied. Samples are prepared and formed into 1 inch width (25.4 mm), and 5 mil thick pieces. These individual pieces are placed in the Instron machine noted earlier, and are elongated or pulled to a distance to represent an elongation equal to 40% and in a latter test, 80% of its unstressed length, for a period of 30 seconds, relaxed for 60 seconds, and then exposed to the same stress for 30 seconds. Data of the force of recovery of the individual samples is collected at the beginning of each pull, and just prior to the end of each of the 30 second holding cycles. The maximum tensile strength is measured at the beginning of the first cycle, and the "percent recovery" is calculated as follows:

$$\frac{\text{Tensile strength following the second 30 sec holding cycle}}{\text{Tensile Maximum}} \times 100 = \% \text{ recovery}$$

The following approximate results in Table IV are believed possible in accordance with the above:

TABLE IV

| Percent Coupled S-I-S | Percent Recovery | Tensile Maximum |
|---|---|---|
| 100% | 78% | 32 grams |
| 90% | 73% | 27 grams |
| 80% | 73% | 26 grams |
| 70% | 67% | 24 grams |
| 60% | 64% | 21 grams |

Adhesives 1–5 further are believed to have a tensile strength of at least 5 psi at about 40% elongation at about 25° C.

Rate of Recovery of the Adhesive is measured on samples of the preferred adhesive. A first rheometric test can be performed by employing a Rheometer marketed under the trade designation RDA 700 by Rheometrics, Inc. of Piscataway, N.J. in its stress relaxation test mode. In this test, the sample to be tested is positioned between opposing plates and one of the plates is rotated about 180° relative to the other plate, which is stationary. This rotation represents about a 50% rotation deformation of the sample. The force of rotation is then released and the residual energy of the recovering sample is then measured, each second, for about a 60 second period. In this particular test, a fully recovered sample is arbitrarily given a $0.01 \times 10^3$ dynes/cm$^2$ per second or less recovery rate. The approximate times that are believed it takes to realize a fully relaxed sample following deformation are noted as follows:

1. Adhesives 1, 2, 4 and 5—11 seconds
2. Adhesive 3—less than 1 second

Uniform samples of the compositions of Adhesives 1–5, above, are prepared and an initial force is placed on each of the samples, thereby rotatingly deforming the samples by about 50%. For calculation purposes, a base line stress is taken following a period of about 60 seconds of relaxation. Any stress remaining in the samples following this recovery period is believed negligible. The amount of force or residual energy remaining in the individual samples following this deformation is collected during each second, for a period of about 60 seconds. Thereafter, the total energy storage of each of the samples is calculated using the formula:

$$\text{Energy Storage} = \left( \frac{\text{dynes/cm}^2}{\text{second}} \right) \times (60 \text{ seconds}) + \left( \begin{array}{c} \text{residual energy exhibited} \\ \text{during the 60 second test} \end{array} \right)$$

Assuming a perfectly elastic sample, the amount of residual energy remaining in a sample following the release of the deformation force would be zero. It is believed, therefore, that as the residual energy values for each of the samples near zero, the elastic recovery properties of the samples should improve. After about 60 seconds of relaxation, the total system energy for each of the samples can be calculated and it is believed that the approximate results are the following:

1. Adhesive 1 - - - $5.924 \times 10^3$ dynes/cm$^2$;
2. Adhesive 2 - - - $4.591 \times 10^5$ dynes/cm$^2$;
3. Adhesive 3 - - - $0.01 \times 10^5$ dynes/cm$^2$;
4. Adhesive 4 - - - $4.809 \times 10^5$ dynes/cm$^2$; and
5. Adhesive 5 - - - $4.804 \times 10^5$ dynes/cm$^2$.

The above is provided for illustration purposes and is not intended to be limiting of the type or nature of the adhesive of the present invention.

The Absorbent Material of the Core

The absorbent material employed in the core of the present invention may be any suitable absorbent material, such as those readily employed and already known in the art (e.g., without limitation, those discussed previously). Likewise, the absorbent material may be employed in any suitable form or aggregation. Examples of such forms include, without limitation, particulates, sponges (e.g., open or closed cell foams), continuous fibers, discrete-length fibers, or the like.

As previously discussed, in a preferred embodiment, the absorbent material is employed as a plurality of particulates, having one or more dimensions ranging from about 0.10 mm to about 6.4 mm, and more preferably about 0.5 mm to about 1.80 mm. In general, the particulates of absorbent material have surface characteristics rendering them compatible for bonding satisfactorily with the stretchable binder material. The particulates may be any shape. In a highly preferred embodiment, the particulates are generally cubic or rectangular prism-like in shape, or have generally cubic or rectangular prism-like portions. Other sizes or shapes (e.g., without limitation, spherical, elliptical, or irregular shapes) may be employed. In another embodiment, the particulates may be generally elongated in nature, or they may be of another suitable shape so that when they absorb a liquid, they will expand in one or more pre-selected directions. The particulates may be substantially all of the same size and shape. Alternatively, they may be a plurality of different sizes or shapes. The size and shape may be varied to take into account such factors as the desired thickness of the overall diaper configuration, or the direction of expansion of the particulates when they have absorbed a fluid.

The absorbent material may be provided already in the ultimate desired size and shape, e.g., as previously fabricated particulates. Alternatively, it may be provided in another suitable form such as, without limitation, as part of a sheet, which may be used as-is, or otherwise cut, ground, or processed (e.g., by relatively low energy techniques) to obtain the desired form.

In one highly preferred embodiment, the absorbent material employed in the core of the present invention is a polymeric foam absorbent material, and more specifically, a hydrophilic, flexible open-celled structure foam material particulate. In general, these materials are characterized in that they have a pore volume of from about 12 to about 100 mL/g, and a capillary suction specific surface area of from about 0.5 to 5.0 m$^2$/g. These materials also exhibit a resistance to compression deflection such that a confining pressure of 5.1 kPa produces after 15 minutes a strain of from about 5% to about 95% compression when the material is saturated at 37° C. to its free absorbent capacity with synthetic urine.

One particularly preferred example of such a material is a material referred to herein as "foam absorbent material" ("FAM"). For additional information about this type of material, reference should be made to the following, all of which are hereby expressly incorporated by reference: Commonly assigned, presently pending, published (on Mar. 4, 1993) PCT Application Nos. 93/04092, entitled: "Absorbent Foam Materials for Aqueous Body Fluids and Absorbent Articles Containing Such Materials", corresponding to U.S. application Ser. No. 743,839, filed Aug. 12, 1991, now U.S. Pat. No. 5,260,345, issued on Nov. 9, 1993; commonly assigned presently pending, published (on Mar. 4, 1993) PCT application Ser. No. 93/04113, entitled "Method for Hydrophilizing Absorbent Foam Materials", corresponding to U.S. application Ser. No. 743,951, filed Aug. 12, 1991 (now abandoned) and U.S. application Ser. No. 08/55,419, filed Apr. 30, 1993; commonly assigned presently pending, published (on Mar. 4, 1993) PCT application Ser. No. 93/04115, entitled "Method for Hydrophilizing Absorbent Foam Materials", corresponding to U.S. application Ser. No. 743,838, now abandoned, filed Aug. 12, 1991; and commonly assigned, presently pending U.S. application Ser. No. 989,270, now U.S. Pat. No. 5,387,207, entitled: "Thin-Until-Wet Absorbent Foam Materials for Aqueous Body Fluids and Process for Making Same", filed Dec. 11, 1992. All of the above applications (U.S. and PCT applications) are hereby expressly incorporated by reference.

It will be appreciated, upon study of such literature as U.S. Pat. No. 5,149,720, hereby expressly incorporated by reference, that FAM is also functional in its sheet form. Thus, it is possible to provide and use FAM in its sheet form or as a film, rather than as particulates.

Other conventional absorbent materials, without limitation, may be used in combination with or in place of a FAM, such as an absorbent gelling material or superabsorbent materials dispersed in a mat of discrete-length (or straight) cellulose fibers or chemically modified cross-linked cellulose fibers. Polyethylene terephthalate fibers may also be employed.

The absorbent materials may be employed in any suitable form such as, without limitation, patch, insert, mat laydown, discrete sheets or layers, or homogeneous blends of one or more combinations of absorbent materials.

The amount of absorbent material (examples discussed previously) that is employed in the absorbent core of the present invention will vary depending upon factors such as, without limitation, the desired size and shape of the diaper and core, which is dictated, in turn, by the size and anatomy of the intended user. The skilled artisan will appreciate that various other factors weigh into the anatomy of the intended user, including but not limited to physical dimensions, geographical location, biological age, or culture. Other considerations factoring into the amount of absorbent material include the absorptive capacity of the absorbent materials used; cost, pricing, or value considerations; or processing, machinery or other mechanical equipment capability and production requirements.

The absorbent material may be distributed generally uniformly throughout a network of the binder material or in certain preselected regions. The type, amount, density, particle size, or distribution of the absorbent material may vary from layer to layer within a multilayer structure, or from location to location within a monolithic structure. In a preferred embodiment, without limitation, where particulates of the absorbent material are employed, they are distributed within the core in either a homogeneous blend of different absorbent materials that respectively function as one or more of acquisition, distribution or storage materials or a layering of those same materials, as discussed previously.

Without intending to be limited hereby, a detailed description of a preferred absorbent material, including its method of manufacture can be found in U.S. Pat. No. 5,260,345, issued Nov. 9, 1993, and hereby expressly incorporated by reference.

Stretchable Diaper Structure

The stretchable absorbent core of the present invention (including any of the core embodiments depicted in FIGS. 1–3) may be readily employed in a number of applications where stretchability and absorbency is desired, particularly in diaper applications. For instance, one preferred embodiment is a stretchable diaper including a core having at least one stretchable region. As shown in FIG. 1B, a core, such as (without limitation) the core 10 of FIGS. 1 and 1A is sandwiched between a topsheet 24 and a backsheet 26, thereby defining a diaper 28. The topsheet 24 preferably is liquid permeable, and preferably includes a stretchable portion over some or all of it. The backsheet 26 preferably is liquid impervious and includes a stretchable portion over some or all of it. Optionally, the topsheet 24, the backsheet 26, or both may not have any substantially elastic portions so that they are not generally stretchable. The entire diaper is cut or otherwise fabricated into a suitable configuration. The diaper is also preferably provided with any conventional suitable closure system such as, without limitation, adhesive tape tabs, mechanical closure tape tabs, fixed position fasteners, or any other means for tensioning the elasticized waistband as are known in the art.

The fastening systems can comprise any attachment means known in the art including pressure sensitive adhesives, cohesive materials, mechanical fasteners, hook and loop type fasteners, or any combination of these or any other attachment means known in the art. Exemplary adhesive tape tab fastening systems are disclosed in U.S. Pat. No. 3,848,594 entitled "Tape Fastening System for Disposable Diaper" (Buell); and U.S. Pat. No. 4,662,875 entitled "Absorbent Article" (Hirotsu et al). Exemplary fastening systems comprising mechanical fastening components are described in U.S. Pat. No. 5,058,247 entitled "Mechanical Fastening Prong" (Thomas); U.S. Pat. No. 4,869,724 entitled "Mechanical Fastening Systems With Adhesive Tape Disposal Means for Disposal of Absorbent Articles" (Scripps); and U.S. Pat. No. 4,864,815 entitled "Disposable Diaper Having an Improved Fastening Device" (Scripps). An example of a fastening system having combination mechanical/adhesive fasteners is described in U.S. Pat. No. 4,946,527 entitled "Pressure-Sensitive Adhesive Fastener and Method of Making Same" (Battrell). Each of these patents are incorporated herein by reference.

Process and Apparatus for Making Stretchable Absorbent Core

The stretchable absorbent core of the present invention is made according to a process including the steps of providing the absorbent material and contacting the absorbent material with a stretchable binder material for forming a stretchable mat-like network that incorporates the absorbent material therein. More particularly, a process is employed to manufacture a continuous mat-like web of the stretchable core material and includes the steps of supplying a stream of the absorbent material in a particulate form; delivering and injecting at least one stream of an elastomeric adhesive into the particulate stream; and laying down the resulting mat-like web. The molten elastomeric adhesive is delivered for injection into the absorbent particulate stream by meltblown processing as a stream of heat-fusible microfibers or filaments which, upon injection and laydown, yield a randomly tangled mat-like network within which the particulated absorbent material is dispersed.

Specifically, the process steps of the present invention includes providing the absorbent material in its desired amount, size and configuration. In a preferred embodiment where the absorbent material is provided in a particulated form, the particulates may be pre-fabricated or may involve a step of cutting, grinding or otherwise breaking up a sheet, film or other agglomeration of the absorbent material into the desired particle size and/or shape. For instance, in an embodiment where particulates of a generally rectangular prism shape are employed, the particulates are cut in generally transverse and longitudinal directions of the sheet or film from a suitable thickness sheet or film of the absorbent material. Any suitable cutting apparatus or technique may be employed. In operation, the particulated absorbent material is supplied at a predetermined flow rate and velocity for establishing a continuous stream thereof.

Further process steps include delivering and injecting a desired amount of the binder material in molten form into a stream of the absorbent material. In a preferred embodiment, the binder material is a hot melt adhesive having one or more elastomeric components that is meltblown for producing one or more streams of fibers or filaments which are subsequently injected and applied to the absorbent material stream. Thereafter, the resulting dispersion of the absorbent material in a randomly entangled network of thermally fused fibers is laid down to form a continuous mat-like web of the stretchable core material.

Figure 4:
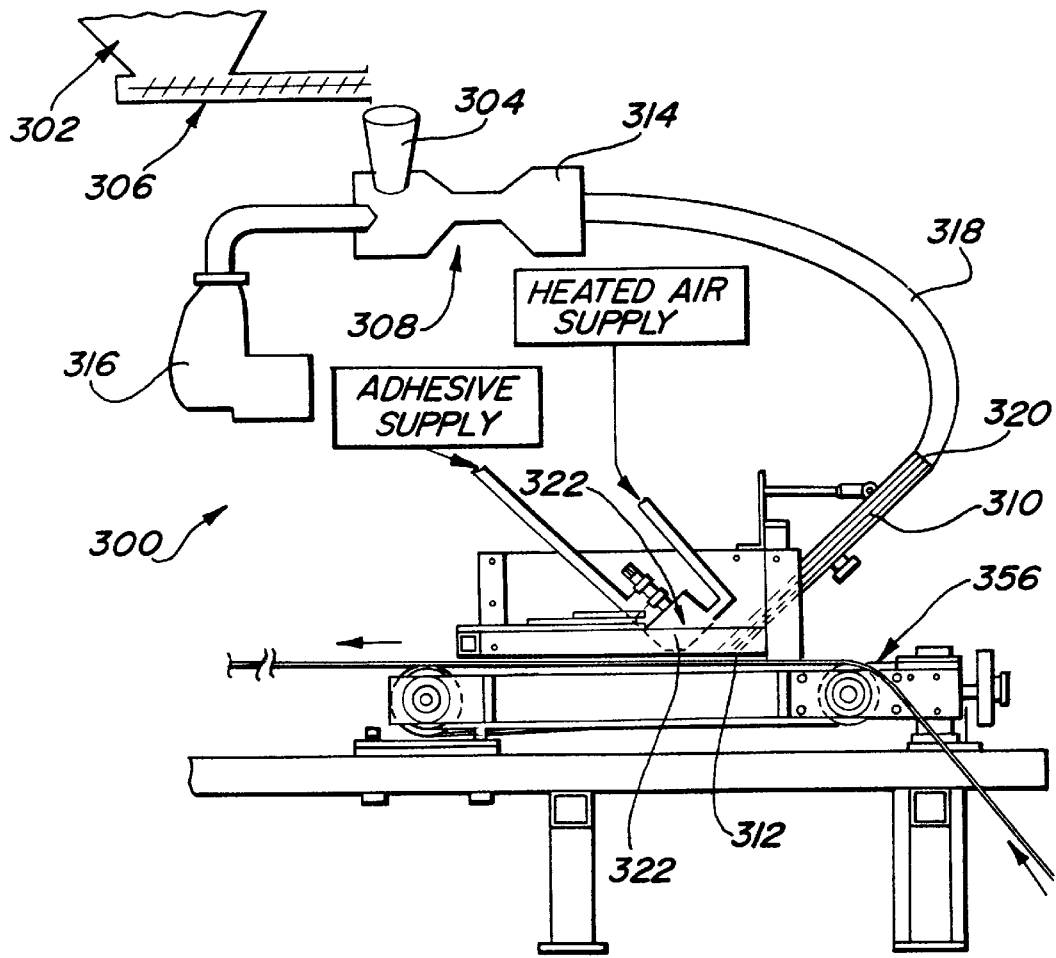
FIG. 4 is a side elevation view of a preferred apparatus for manufacturing a mat-like web for use as a stretchable core material.
Figure 5:
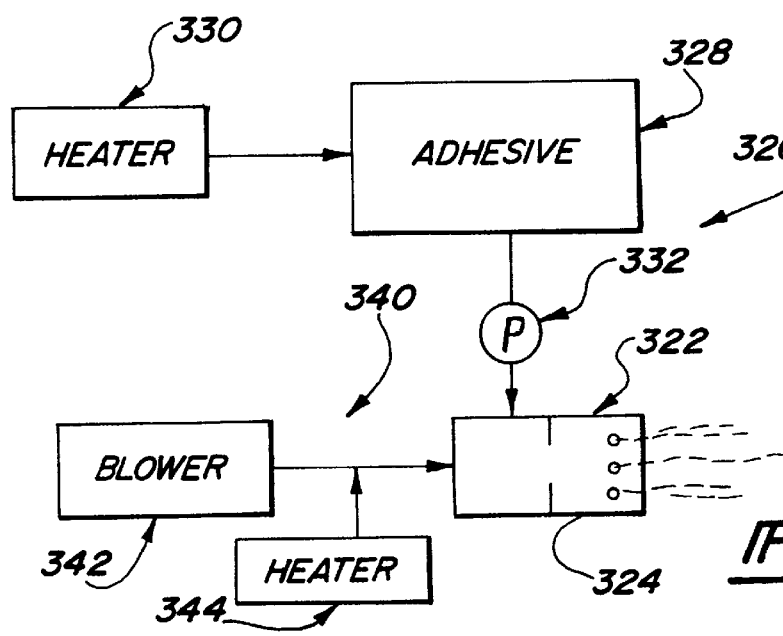
FIG. 5 is a schematic view of an apparatus for delivering meltblown elastomeric adhesive to an injection segment of the apparatus of FIG. 4.

Referring to FIG. 4 and FIG. 5, an apparatus 300 according to a preferred embodiment of the present invention is shown. Apparatus 300 is operable to deliver, inject and apply the stretchable binder material to the absorbent material for forming the mat-like web of stretchable core material. Apparatus 300 is further operable for laying down the stretchable mat-like web on a continuous liquid permeable or porous, stretchable web to form a generally bonded mat-like web of the stretchable core material. Absorbent material (which may be of a generally uniform composition, or include two or more different compositions) is collected in a suitable container, such as a bulk storage hopper 302, and is dispensed therefrom for processing in the desired quantity. As will be appreciated, the quantity and rate at which the absorbent material is dispersed will vary depending on such factors as, without limitation, the desired size, shape and performance characteristics of the stretchable core, and other factors such as, without limitation, machinery processing capability, production requirements or the like.

In a preferred embodiment, a metered quantity of the absorbent material within hopper 302 is conveyed and fed into the open end of a generally vertically-oriented funnel 304 via a suitable feeder apparatus, such as a screw-type feeder 306. Where the absorbent material is particulated, feeder 306 is further operable to aid in keeping individual particulates of absorbent material from collecting and adhering together prior to being contacted with the adhesive material and to maintain a generally constant feed rate of particulates to the funnel 304. As seen from FIG. 4, the discharge end of funnel 304 communicates with an accelerator arrangement 308 that is operable for forcibly propelling the absorbent material through a delivery chute 310 so that they subsequently encounter at least one molten stream (preferably a plurality of paths) of the stretchable binder material being introduced for contacting the particulates. More specifically, between funnel 304 and a discharge end 312 of the delivery chute 310 is a venturi-type or eductor (ejector) 314 and a compressor or blower 316 that cooperate to forcibly propel the particulates toward the discharge end 312 of the delivery chute 310. As seen, a conduit or suitable ductwork 318 interconnects a discharge end of the eductor 314 with an inlet end 320 of the delivery chute 310. As will be appreciated, the volumetric flow rate and pressure of the air supplied by blower 316 into the inlet end of eductor 314 can be varied depending on the discharge parameters (i.e., particulate stream velocity and density) required for the stream of absorbent material exiting the discharge end 312 of the delivery chute 310. By way of example, without limitation, suitable equipment for the above includes a FUJI compressor Model No. VFC503A-7W available from Fuji Elec. Co. of Lincoln Park, N.J., U.S.A., in combination with a FOX Venturi Eductor Series 300-SCE available from Fox Valve Dev. Corp. of Dover, N.J., and a KATRON F-1 Twin Screw Feeder available from K-Tron Corp. in Pitman, N.J. The skilled artisan will readily appreciate how the above-noted equipment, or equivalents thereof, can be operating within known parameters to provide the required stream of absorbent material at the discharge end 312 of the chute 310.

In a particularly preferred embodiment, the stream of absorbent material discharged from the discharge end 312 of the delivery chute 310 is contacted by one or more fibrous streams of a meltblown elastomeric adhesive, such as that previously described, which are discharged from corresponding extruder dies or glue heads 322. As is conventionally known, the term "meltblown" is generally descriptive of a process used to form a random non-woven network of entangled heat-fusible fibers or filaments. In operation, a low viscosity, molten polymer is extruded through a series of small discharge orifices formed in the extruder die or glue head nozzle to define a series of continuous fibers or filaments. These filaments are immediately exposed to a heated, high velocity airstream for disrupting or attenuating the flow of molten polymer. Due to the flow disruption caused by such air impingement, the fibers are formed into a random, entangled network of heat-fused filaments or fiber; upon deposition on a continuously moving collecting screen or roll.

As illustrated in FIGS. 5 and 5A, a typical stream of fibers or filaments of the elastomeric adhesive emerges from a discharge nozzle 324 of the glue head 322 and which is fed by an adhesive delivery system 326 for supplying and discharging the meltblown adhesive. The adhesive delivery system 326 is adapted to discharge fibers or filaments of the meltblown adhesive at a predetermined adhesive temperature, flow rate, viscosity, pressure, velocity, injection angle, and forming distance. The adhesive delivery system 326 preferably includes a vat 328, for storing the meltblown adhesive, and a suitable heater 330 in thermal communication with the vat 328, for heating the meltblown adhesive to achieve and maintain a desired adhesive temperature and viscosity for facilitating meltblown processing of the adhesive. Accordingly, in a preferred embodiment, the temperature of the meltblown adhesive is maintained for discharge from nozzle 324 in the range of about 138° C. to about 260° C. and more preferably in the range of about 149° C. to about 177° C., at a viscosity in the range of about 10,000 cps to about 50,000 cps, and more preferably in the range of about 20,000 cps to about 35,000 cps.

With continued reference to FIGS. 5 and 5A, the adhesive delivery system 326 is also shown to include a pumping apparatus 332, such as a gear pump, for delivering the molten adhesive at a suitable flow rate (e.g., in one embodiment, about 200 g/min to about 240 g/min) and pressure from the heated vat 328 into a central distribution chamber 334 of the glue head nozzle 324 from which it is subsequently discharged as a filament stream through a series of spaced die tip bores 336 and corresponding orifices 338 for contacting (i.e., injection into) the stream of absorbent material. An air delivery system 340 is provided for supplying and discharging heated, pressurized air to the glue head nozzle 324. Preferably, air delivery system 340 includes a source of pressurized air, such as blower 342, and a suitable heater 344 for heating the melt blown air discharged from the blower 342 and delivered to the glue head nozzle 324 in a preferred range of about 163° C. to about 246° C. The heated, pressurized air is supplied to an air chamber 346 of the glue head nozzle 324 via inlet port 347. As seen, air chamber 346 communicates with a series of spaced air passageways 348A and 348B formed on opposite sides of die tip orifices 338. The high velocity heated airstream exiting the air discharge orifices 350A and 350B is adapted to attenuate or disrupt the flow of the molten elastomeric adhesive upon impingement therewith. An air plate segment 352 of glue head nozzle 324 is adapted to form an elongated channel 353 for directing the heated airstream relative to the molten adhesive as it is extruded through orifices 338. In operation, the air has a carrier function for conveying the filaments into contact with the absorbent material (e.g., particulates), and ultimately depositing the network of adhesive filaments and absorbent material. It will be understood that the structure shown in FIG. 5A is merely exemplary of but one glue head device available in the art. By way of example, without limitation, suitable equipment for the above process includes melt blowing equipment from J&M Laboratories, Inc. of Dawsonville, Ga., (i.e., Model AMBI-2-1; Model AMBI-45-3; and Model AMBI-1.5-1). Other suitable melt blowing equipment is disclosed in U.S. Pat. Nos. 5,145,689, 5,102,484, and 5,236,641, hereby incorporated by reference. Again, the skilled artisan will appreciate that such known and/or commercially-available equipment can be operated within known operating parameters to provide a desired glue temperature, flow rate, viscosity, pressure and forming distance for the particular adhesive being used.

Immediately upon discharge from the die tip orifices 338, the stream of meltblown adhesive is taffy-like in nature, and will plastically deform in response to the attenuation forces exerted thereon by the heated meltblown air. In one embodiment, the die tip orifices 338 are generally circular and have a diameter of about 0.5 mm to about 1.02 mm, with typical air gaps between adjacent orifices of about 0.05 mm to 0.25 mm. In view of the impingement forces applied to the meltblown adhesive extruded by the heated high velocity air, it is possible that, before the filaments contact the absorbent material, each filament will undergo a diameter reduction in the range of about one-one hundredth of the diameter it had immediately upon discharge for the nozzle 324. Preferably, the adhesive filaments that are meltblown will be distributed such that, where the absorbent material is particulated, each particulate of absorbent material is in contact (i.e., entangled) with, or in close proximity to, a filament (e.g., upon swelling with liquid the particulate will come into contact with a fiber).

The source of pressurized air may be any suitable source, such as blower 342, and is preferably compressed air that is delivered and blown in suitable amounts (e.g., in one embodiment, the air flow is about 0.5 SCFM (14.15 liters/min) to about 4 SCFM (113 liters/rain) per inch of die tip width) over a predetermined amount of time, to build up a suitable pressure for assisting in drawing the meltblown adhesive through the discharge orifices 338 of the nozzle 324 in filament form and into subsequent contact with the stream of absorbent material. By way of example, for blowing an amount of about 240 g/min of adhesive, at a glue temperature of about 163° C., through generally circular die tip orifices having a diameter of about 0.76 mm, with a residence time within the glue head 322 of approximately 80 to 150 milliseconds, a volume of air of about 36.8 liters/min is supplied to the nozzle 324 at a temperature of about 190.6 to about 218° C.

Preferably, one or more of the extruder dies or glue heads 322 (with each containing one or more nozzles 324) are employed during the melt blowing step and are connected to either the same adhesive delivering system 326 and air delivery system 340, or respectively to a plurality of substantially similar systems. In the operation of the apparatus, embodiment shown in FIG. 4, a pair of glue heads 322 (one shown) are aligned and spaced apart from each other, (e.g., by about 38 mm on center for the present preferred embodiment). Preferably, the nozzle 324 for each of the glue heads 322 is positioned with sufficient spacing for the absorbent material to be fed for dispersion and contact with the meltblown adhesive that is blown. In a still further preferred embodiment, the nozzle 324 of each of the glue heads 322 is disposed generally at an injection angle of about 90° relative to the direction of flow of the absorbent material stream, so as to be aimed generally downward, and at a forming distance of about 25.4 mm to about 50.8 mm from the stream. When the nozzles 324 are disposed in this orientation relative to the flow of absorbent material, the resulting "vector" of the meltblown adhesive upon discharge from the nozzles 324 is generally directly downward in the same direction as the flow of absorbent material. Additionally, cooling air can be provided, if necessary, to quench the fibers upon deposition of the mat-like web of stretchable core material onto a laydown conveyor 356.

Preferably, a vacuum source (not shown in FIG. 4, see FIG. 6) is provided for generating a negative pressure condition above laydown conveyor 356. More preferably, laydown conveyor 356 has a predetermined number of vacuum holes (not shown in FIG. 4, see FIG. 6A) of a predetermined diameter for facilitating the draw of negatively pressured air therethrough. Therefore, the speed and volume (i.e., feed rate) of the combined absorbent material/fibrous adhesive material relative to the speed of laydown conveyor 356, the vacuum level drawn through laydown conveyor 356, and the laydown width/shape are considerations for determining the thickness (caliper or density) of the resulting mat-like webbing. By way of example, without limitation, for laydown of a webbing having a thickness of about 3.8 mm and a width of about 12.7 mm, where the absorbent material is particulated, a feed rate of absorbent material particulates that are about 1.5 mm in diameter through the discharge end 312 of the delivery chute 310 of about 5450 g/min is combined with the feed rate of about 240 g/min for the adhesive extended through the nozzle 324 with the laydown conveyor 356 moving at a linear speed of 270.5 meters/min. Furthermore, an adhesive temperature of about 162.7° C. and a hot air temperature of about 190.6° C. at operating pressure of about 1.1 Kg/cm$^2$ and air flow at about 36.8 liters/min using die tip orifices 338 having a diameter of about 0.76 mm and an air gap of about 0.18 mm at a forming distance of about 25.4 mm is used for forming a fiber size on the order of about 0.01 mm.

In a particularly preferred embodiment, the dynamics accompanying the flow of the meltblown adhesive in combination with the flow of particulates of the absorbent material will result in a generally random network (e.g., a matrix) of meltblown fibers or filaments, many of which will adhere to other fibers or filaments, to the particulates, or to both. Thus, a continuous web of a mat-like structure or a meltblown fiber network will preferably result having a dispersion of the particulates therein. The spacing of particulates is preferably such that it will permit the particulates to make optimum use of their individual and collective functional characteristics. To this end, for every gram of meltblown adhesive that is blown, preferably about 90 g to about 98 g, and more preferably about 94 g to about 96 g of particulates of the absorbent material are contacted and become arranged in a generally uniform dispersion having a concentration of about 0.07 g/cm$^3$ to about 0.16 g/cm$^3$ and more preferably 0.09 g/cm$^3$ to about 0.14 g/cm$^3$ of absorbent material within the meltblown fiber network.

Following the above-described process for dispersing the absorbent material within the meltblown adhesive fiber network, the resulting mat-like web formed thereby is preferably laid down on a substrate material. More preferably, the substrate material is, but not limited to, the stretchable topsheet or stretchable backsheet for the diaper, or a suitable envelope material.

With particular reference to FIG. 6., an alternative preferred embodiment for an apparatus 400 is shown which is likewise operable for forming a continuous mat-like web of the stretchable core material. Apparatus 400, like apparatus 300, is generally adapted to deliver, inject and apply the stretchable binder material to a stream of the absorbent material. Due to the utilization of common or substantially similar equipment, reference numerals previously used for identifying various subsystems of apparatus 300 are likewise used herein to identify corresponding subsystems of apparatus 400.

The absorbent material (which preferably is particulated, and may be of a generally uniform composition, or include two or more different compositions) is collected to bulk storage hopper 302 and is dispensed therefrom for processing in the desired quantity. The quantity and rate of dispensing will vary depending on such factors as, without limitation, the desired size, shape and performance characteristics of the core, and other factors such as, without limitation, machinery processing capability, production requirements or the like. In the preferred embodiment shown in FIG. 6, the absorbent material is delivered from the hopper 302 and when the absorbent material is particulated, vibrated at one or more vibrating sites 401 by a vibrating conveyor 402 to help aid in keeping the individual particulates from collecting and joining together prior to being contacted with the binder material while maintaining a generally constant feed rate of the vibrated particulates that are ultimately conveyed to a site near the location where particulate stream is contacted with the binder material. This entails gravitationally feeding the vibrated particulates from the vibrating conveyor 402 into the open end of a funnel portion 404 of a vacuum chute 406 so that the particulates subsequently encounter at least one stream (preferably a plurality of paths) defined by the stretchable binder material. More preferably, the vacuum chute 406 is connected to a first suitable vacuum source 412 for generating a negative pressure condition therein which assists in drawing the particulates of absorbent material downwardly.

Specifically, in a particularly preferred embodiment shown in FIG. 6, vibrated particulates of absorbent material are gravitationally fed through the vacuum chute 406 between at least one or more streams of a meltblown elastomeric adhesive, such as that previously described and which are discharged from an opposed pair of glue heads 322. As discussed relative to FIGS. 5 and 5A, a typical stream of the adhesive emerges from the discharge nozzle 324 of the glue heads 322 which is fed by the adhesive delivery system 326, and attenuated by the heated pressurized air supplied by the air delivery system 340. As noted, the adhesive delivery system 326 is adapted to discharge the meltblown adhesive at a predetermined adhesive temperature, pressure, flow rate, viscosity, injection angle and forming distance.

Accordingly, in a preferred embodiment, the temperature of the meltblown adhesive is maintained in the range of about 138° C. to about 260° C. and more preferably about 149° C. to about 177° C., for a viscosity in the range of about 10,000 cps to about 50,000 cps, and more preferably about 20,000 cps to about 35,000 cps. Similarly, the pumping apparatus 332 delivers the meltblown adhesive, at a suitable rate (e.g., about 200 g/min to about 240 g/min), from the heated vat 328 into the distribution chamber 334 of each of the glue heads 322 from which the meltblown adhesive is subsequently discharged as a fibrous stream for contacting the absorbent material. As also noted, the air delivery system 340 provides means, such as the heater 344, for maintaining the meltblown air discharged from blower 342 in a range of about 163° C. to about 246° C. Thereafter, the heated pressurized air is supplied through air chamber 346, air passageways 348A and 348B to air outlets 350A and 350B for providing the attenuating high velocity airstream discussed above. By way of example, but without limitation, for blowing an amount of about 240 g/min of adhesive, at a glue temperature of about 163° C., through a generally circular die tip orifice 338 having a diameter of about 0.76 min, a volume of air of about 368 liters/min heated from about 190.6° C. to about 218° C. is blown into the air chamber 346 of glue heads 322.

In operation of the apparatus 400 shown in FIG. 6, the glue heads 322 are positioned so that their discharge orifices 338 are in an opposed facing orientation. In a still further preferred embodiment, the nozzles 324 of the opposed glue heads 322 are disposed generally at about a 45° angle relative to the direction of flow of the absorbent material stream, so they are aimed generally downward, and at a forming distance of about 25.4 mm to about 50.8 mm from the absorbent material. Again, when the nozzles 324 are disposed in this orientation relative to the flow of absorbent material, the resulting "vector" of the blown adhesive upon discharge from the nozzle, is generally directly downward in the same direction as the flow of absorbent material.

It will again be appreciated that the dynamics accompanying the gravitational flow of the absorbent material, combined with melt blowing of the adhesive, will result in a generally random network (e.g., a matrix) of meltblown fibers or filaments, many of which will adhere to other fibers or filaments to the absorbent material, or to both. Thus, a continuous web of a mat-like structure will preferably result having a random dispersion of the absorbent material therein. When the absorbent material is particulated, the spacing of particulates is preferably such that it will permit the particulates to make optimum use of their individual and collective functional characteristics. To this end, for every gram of meltblown adhesive that is blown, preferably about 90 g to about 98 g, and more preferably about 94 g to about 96 g of absorbent material particulates are contacted and become arranged in a generally uniform dispersion having a concentration of about 0.07 g/cm$^3$ to about 0.16 g/cm$^3$ and more preferably 0.09 g/cm$^3$ to about 0.14 g/cm$^3$ of absorbent material particulates within the meltblown fiber network.

Following the above-described process for dispersing the absorbent material within the meltblown fiber network, the mat-like continuous web formed thereby is preferably laid down on a substrate material. Again, the substrate may be, but is not limited to, the stretchable top sheet or stretchable backsheet, or a stretchable envelope material. Preferably, the vacuum source 412 associated with the vacuum chute 406, downstream of the glue heads 322 is commonly utilized to generate a negative pressure condition within a laydown chute 410 and above laydown conveyor 356. In this manner, the position and orientation of the substrate web is maintained on laydown conveyor 356 for deposition of the meltblown network of stretchable adhesive fibers and absorbent material thereon. As noted, laydown conveyor 356 preferably has a predetermined number of vacuum holes 414 (shown in FIG. 6A) for facilitating the draw of negatively pressurized air therethrough supplied by a second suitable vacuum source 416. As can be appreciated by skilled artisans, first and second vacuum sources 412 and 416 can be a common vacuum source or separate vacuum sources. Therefore, the speed and volume (i.e., feed rate) of the combined absorbent material/fibrous adhesive material discharged through laydown chute 410 relative to the speed of laydown conveyor 356, the vacuum level drawn through laydown conveyor 356, and the laydown width/shape are considerations for determining the thickness (caliper or density) of the mat-like webbing. It is to be understood that the exemplary laydown parameters set forth for apparatus 300 are likewise applicable to apparatus 400.

As previously discussed, there are various ways to prepare a core having a plurality of different core types, or including a patch. In one preferred embodiment, where the various layers are stretchable absorbent layers, the layers can be made according to the above-described process, where a separate apparatus (each performing substantially the same process, with certain of the above variables changed as desired to achieve the desired properties in the patch) is employed for each of the respective layers. The layers could be made generally simultaneously at each apparatus and then assembled at a downstream location. Alternatively, they can be made in series or set of progressive steps, with each successive layer being laid down on a previously made layer. Furthermore, they could be mixed as a homogeneous blend and delivered to produce x/y/z axis profiling.

In one embodiment, the resulting mat-like web of absorbent material and meltblown adhesive may be in a rectangular arrangement. In another embodiment, after entangling the absorbent material (e.g., which is particulated) with the meltblown adhesive, the resulting combination may be cut and shaped into a final core shape for subsequent delivery and lamination as a core between a topsheet and a back sheet for forming a diaper. Conventional diaper forming techniques may thus be employed.

Preferably, the stretchable absorbent core is laid down between a web for a topsheet (of the type previously described) and a web for a backsheet (also of the type previously described). The web for the topsheet and the web for the backsheet preferably are conveyed opposite each other prior to the stretchable absorbent core being introduced therebetween. After the stretchable absorbent core is introduced, the respective webs are brought closer together until they each are in contact with the core. A resulting assembly of layers (i.e., top sheet, core and backsheet) is compressed, such as by passing it between two nip rollers that are spaced apart by a distance as low as about one-half the thickness of the diaper assembly. Preferably, the resulting thickness of the assembly of layers has a thickness ranging from about 2.85 mm to about 5.12 mm. Of course, it may also be thicker or thinner.

Construction of the diapers is finished by conventional steps of forming leg cutouts, joining the topsheet to the back sheet (thereby encapsulating the core), and adding suitable fasteners.

Although the invention has been described with particular reference to certain preferred embodiments thereof, variations and modifications can be effected within the spirit and scope of the following claims.

What is claimed is:

1. A method for making a stretchable absorbent core, comprising the steps of:
   (a) providing a first material capable of absorbing a liquid;
   (b) providing a second material capable of adhering to said first material, said second material being capable of being formed into a first configuration having a predetermined dimension in each of the x, y, and z directions that can be stretched by application of a force to achieve a second configuration, and said second material being capable of returning substantially to said first configuration after removal of said force;
   (c) contacting said first material with said second material for incorporating said first material into a stretchable network of said second material; and
   (d) forming a absorbent core from said stretchable network of said second material.

2. The method according to claim 1 wherein said first material is a foam absorbent material.

3. The method according to claim 2 wherein said first material includes a plurality of foam absorbent material particulates.

4. The method according to claim 1 wherein said second material is an elastomeric, hot-melt pressure-sensitive adhesive.

5. The method according to claim 1 wherein said absorbent core is capable of absorbing liquid in an amount of at least about 1900% of its overall weight, as measured when dried, and is capable of stretching to at least about 100% to 200% of its original dimensions in at least said x and y directions.

6. The method according to claim 1 wherein said contacting step includes directing a stream of said second material against a stream of particulates of said first material.

7. The method according to claim 1 wherein said second material includes an A-B-A-type copolymer, wherein said B portion of said copolymer is an elastomeric material.

8. The method according to claim 7 wherein said A-B-A-type copolymer is styrene-isoprene-styrene.

9. The method according to claim 7 wherein said A-B-A-type copolymer is styrene-butadiene-styrene.

10. An apparatus for manufacturing a stretchable absorbent article, comprising:
    (a) means for providing an absorbent material; and
    (b) means for entangling a stretchable hot-melt adhesive material with said absorbent material to form a stretchable network of said stretchable material incorporating said absorbent material;
    wherein said entangling means is capable of delivering said stretchable hotmelt adhesive material at a rate of about 200 g/min to about 240 g/min.

11. The apparatus according to claim 10 wherein said entangling means includes means for forming said stretchable material into a fiber and means for dispersing said fiber randomly in said network with a plurality of foam absorbent material particulates.

12. The apparatus according to claim 10 wherein said stretchable network is laid down onto a stretchable carrier substrate.

13. The apparatus according to claim 10 further comprising means for transporting said stretchable network to a downstream operation.

14. The apparatus according to claim 10 wherein said providing means includes means for vibrating said absorbent material prior to delivery to said entangling means.

15. The apparatus according to claim 10 wherein said providing means further includes means for applying a negative pressure to draw or accelerate said absorbent material downward through said entangling means.

16. An apparatus for manufacturing a stretchable absorbent article, comprising:
    (a) a first delivery device for dispensing a first material capable of absorbing a liquid; and
    (b) a second delivery device having at least one discharge orifice for forming a filament having a sectional area at discharge of about 0.20 mm$^2$ to about 0.82 mm$^2$ for dispensing a second material capable of adhering to said first material;
    wherein said second material is entangled with said first material at said second delivery device to form a stretchable network.

17. The apparatus according to claim 16 further comprising means for vibrating said first material prior to entanglement with said second material, wherein said first material includes a plurality of foam absorbent material particulates and said second material is an elastomeric, hot-melt pressure-sensitive adhesive.

18. The apparatus according to claim 16 wherein said second delivery device is capable of delivering said second material at a rate of about 200 g/min to about 240 g/min and said stretchable network has a first configuration having a predetermined dimension in each of the x, y, and z directions that can be stretched by application of a force to achieve a second configuration, said stretchable network being capable of returning substantially to said first configuration after removal of said force.

19. The apparatus according to claim 16 wherein said stretchable network is laid down onto a stretchable carrier substrate.

20. The apparatus according to claim 16 further comprising a transporting device wherein said stretchable network is transported to a location downstream from said first and second delivery devices.

* * * * *

UNITED STATES PATENT AND TRADEMARK OFFICE
CERTIFICATE OF CORRECTION

PATENT NO. : 5,858,292 Page 1 of 1
DATED : January 12, 1999
INVENTOR(S) : Jerry L. Dragoo et al.

It is certified that error appears in the above-identified patent and that said Letters Patent is hereby corrected as shown below:

Column 8,
Line 59, after "weight" insert -- ) --.
Line 63, delete "of".
Line 63, "-1.4" should be -- ~1.4 --.

Column 9,
Line 5, after "binder" insert -- . --.

Column 10,
Line 36, "opencelled" should be -- open-celled --.

Column 11,
Line 8, "stricture" should be -- structure --.

Column 12,
Line 13, "300°F." should be -- 325°F. --.
Line 56, "tape" should be -- type --.

Column 15,
Line 29, "Cyana mid" should be -- Cyanamid --.

Column 23,
Line 45, delete ";".

Column 25,
Line 3, "rain" should be -- min --.

Signed and Sealed this

Twenty-eighth Day of January, 2003

JAMES E. ROGAN
*Director of the United States Patent and Trademark Office*